（12） United States Patent
Bailey et al.

(10) Patent No.: US 11,426,123 B2
(45) Date of Patent: Aug. 30, 2022

(54) SYSTEMS, ARTICLES AND METHODS FOR SIGNAL ROUTING IN WEARABLE ELECTRONIC DEVICES THAT DETECT MUSCLE ACTIVITY OF A USER USING A SET OF DISCRETE AND SEPARATELY ENCLOSED POD STRUCTURES

(71) Applicant: META PLATFORMS TECHNOLOGIES, LLC, Menlo Park, CA (US)

(72) Inventors: Matthew Bailey, Kitchener (CA); Stephen Lake, Kitchener (CA); Aaron Grant, Kitchener (CA)

(73) Assignee: Meta Platforms Technologies, LLC, Menlo Park, CA (US)

( * ) Notice: Subject to any disclaimer, the term of this patent is extended or adjusted under 35 U.S.C. 154(b) by 1030 days.

(21) Appl. No.: 14/461,044

(22) Filed: Aug. 15, 2014

(65) Prior Publication Data

US 2015/0051470 A1 Feb. 19, 2015

Related U.S. Application Data

(60) Provisional application No. 61/866,960, filed on Aug. 16, 2013.

(51) Int. Cl.
*A61B 5/00* (2006.01)
*G06F 1/16* (2006.01)
(Continued)

(52) U.S. Cl.
CPC .............. *A61B 5/681* (2013.01); *G06F 1/163* (2013.01); *G06F 3/015* (2013.01); *A61B 5/389* (2021.01); *A61B 5/6898* (2013.01); *A61B 5/7475* (2013.01)

(58) Field of Classification Search
CPC ......... A61B 5/68; A61B 5/6802; A61B 5/681; A61B 5/6831; A61B 5/389; A61B 5/6896; A61B 5/7475; G06F 1/163; G06F 3/015

(Continued)

(56) References Cited

U.S. PATENT DOCUMENTS 1,411,995 A 4/1922 Dull
3,620,208 A 11/1971 Higley et al.
(Continued)

FOREIGN PATENT DOCUMENTS

DE 44 12 278 A1 10/1995
EP 0 301 790 A2 2/1989
(Continued)

OTHER PUBLICATIONS

Brownlee, "Finite State Machines (FSM): Finite state machines as a control technique in Artificial Intelligence (AI)," Jun. 2002, 12 pages.

(Continued)

*Primary Examiner* — Christopher A Flory
(74) *Attorney, Agent, or Firm* — Morgan, Lewis & Bockius LLP

(57) ABSTRACT

Wearable electronic devices that employ techniques for routing signals between components are described. An exemplary wearable electronic device includes a set of pod structures with each pod structure positioned adjacent and physically coupled to at least one other pod structure. The set of pod structures includes multiple sensor pods and at least one processor pod. Each sensor pod includes an on-board sensor to in use detect user-effected inputs and provide signals in response to the user-effected inputs. The signals are serially routed via successive ones of adjacent pod structures by respective communicative pathways until the signals are routed from the sensor pods to the processor pod. A processor on-board the processor pod processes the signals. Systems, articles, and methods for routing electrical signals and/or optical signals, including analog signals and/or digital signals, between pod structures are described.

41 Claims, 5 Drawing Sheets

(51) Int. Cl.
*G06F 3/01* (2006.01)
*A61B 5/389* (2021.01)

(58) Field of Classification Search
USPC .................................... 600/301, 388, 390
See application file for complete search history.

(56) References Cited

U.S. PATENT DOCUMENTS

| | | |
|---|---|---|
| 3,880,146 A | 4/1975 | Everett et al. |
| 4,602,639 A | 7/1986 | Hoogendoom et al. |
| 4,817,064 A | 3/1989 | Milles |
| 5,003,978 A | 4/1991 | Dunseath, Jr. |
| D322,227 S | 12/1991 | Warhol |
| 5,081,852 A | 1/1992 | Cox |
| 5,251,189 A | 10/1993 | Thorp |
| D348,660 S | 7/1994 | Parsons |
| 5,445,869 A | 8/1995 | Ishikawa et al. |
| 5,482,051 A | 1/1996 | Reddy et al. |
| 5,605,059 A | 2/1997 | Woodward |
| 5,683,404 A | 11/1997 | Johnson |
| 6,032,530 A | 3/2000 | Hock |
| 6,184,847 B1 | 2/2001 | Fateh et al. |
| 6,238,338 B1 | 5/2001 | DeLuca et al. |
| 6,244,873 B1 | 6/2001 | Hill et al. |
| 6,377,277 B1 | 4/2002 | Yamamoto |
| D459,352 S | 6/2002 | Giovanniello |
| 6,487,906 B1 | 12/2002 | Hock |
| 6,510,333 B1 | 1/2003 | Licata et al. |
| 6,527,711 B1 | 3/2003 | Stivoric et al. |
| 6,619,836 B1 | 9/2003 | Silvant et al. |
| 6,720,984 B1 | 4/2004 | Jorgensen et al. |
| 6,743,982 B2 | 6/2004 | Biegelsen et al. |
| 6,807,438 B1 | 10/2004 | Brun Del Re et al. |
| D502,661 S | 3/2005 | Rapport |
| D502,662 S | 3/2005 | Rapport |
| 6,865,409 B2 | 3/2005 | Getsla et al. |
| D503,646 S | 4/2005 | Rapport |
| 6,880,364 B1 | 4/2005 | Vidolin et al. |
| 6,927,343 B2 | 8/2005 | Watanabe et al. |
| 6,965,842 B2 | 11/2005 | Rekimoto |
| 6,972,734 B1 | 12/2005 | Ohshima et al. |
| 6,984,208 B2 | 1/2006 | Zheng |
| 7,022,919 B2 | 4/2006 | Brist et al. |
| 7,086,218 B1 | 8/2006 | Pasach |
| D535,401 S | 1/2007 | Travis et al. |
| 7,173,437 B2 | 2/2007 | Hervieux et al. |
| D543,212 S | 5/2007 | Marks |
| 7,265,298 B2 | 9/2007 | Maghribi et al. |
| 7,271,774 B2 | 9/2007 | Puuri |
| 7,333,090 B2 | 2/2008 | Tanaka et al. |
| 7,450,107 B2 | 11/2008 | Radley-Smith |
| 7,491,892 B2 | 2/2009 | Wagner et al. |
| 7,517,725 B2 * | 4/2009 | Reis .................. H01L 21/67132 257/E21.599 |
| 7,558,622 B2 | 7/2009 | Tran |
| 7,596,393 B2 | 9/2009 | Jung et al. |
| 7,618,260 B2 | 11/2009 | Daniel et al. |
| 7,636,549 B2 | 12/2009 | Ma et al. |
| 7,640,007 B2 | 12/2009 | Chen et al. |
| 7,660,126 B2 | 2/2010 | Cho et al. |
| 7,809,435 B1 | 10/2010 | Ettare et al. |
| 7,844,310 B2 | 11/2010 | Anderson |
| 7,870,211 B2 * | 1/2011 | Pascal ..................... H04L 51/36 709/205 |
| 7,925,100 B2 | 4/2011 | Howell et al. |
| 7,948,763 B2 * | 5/2011 | Chuang .................. H05K 1/028 174/254 |
| D643,428 S | 8/2011 | Janky et al. |
| D646,192 S | 10/2011 | Woode |
| 8,054,061 B2 | 11/2011 | Prance et al. |
| D654,622 S | 2/2012 | Hsu |
| 8,170,656 B2 | 5/2012 | Tan et al. |
| 8,179,604 B1 | 5/2012 | Prada Gomez et al. |
| 8,188,937 B1 | 5/2012 | Amafuji et al. |
| D661,613 S | 6/2012 | Demeglio |
| 8,203,502 B1 | 6/2012 | Chi et al. |
| 8,207,473 B2 * | 6/2012 | Axisa .................. B32B 37/185 174/254 |
| 8,212,859 B2 | 7/2012 | Tang et al. |
| 8,355,671 B2 | 1/2013 | Kramer et al. |
| 8,389,862 B2 | 3/2013 | Arora et al. |
| 8,421,634 B2 | 4/2013 | Tan et al. |
| 8,427,977 B2 | 4/2013 | Workman et al. |
| D682,727 S | 5/2013 | Bulgari |
| 8,447,704 B2 | 5/2013 | Tan et al. |
| 8,467,270 B2 | 6/2013 | Gossweiler, III et al. |
| 8,469,741 B2 | 6/2013 | Oster et al. |
| D689,862 S | 9/2013 | Liu |
| D695,454 S | 12/2013 | Moore |
| 8,620,361 B2 * | 12/2013 | Bailey .................. H04L 51/066 455/412.1 |
| 8,624,124 B2 | 1/2014 | Koo et al. |
| 8,704,882 B2 | 4/2014 | Turner |
| 8,777,668 B2 | 7/2014 | Ikeda et al. |
| D716,457 S | 10/2014 | Brefka et al. |
| D717,685 S | 11/2014 | Bailey et al. |
| 8,883,287 B2 | 11/2014 | Boyce et al. |
| 8,895,865 B2 | 11/2014 | Lenahan et al. |
| 8,912,094 B2 | 12/2014 | Koo et al. |
| 8,922,481 B1 | 12/2014 | Kauffmann et al. |
| 8,954,135 B2 | 2/2015 | Yuen et al. |
| 8,970,571 B1 | 3/2015 | Wong et al. |
| 8,971,023 B2 | 3/2015 | Olsson et al. |
| 9,018,532 B2 | 4/2015 | Wesselmann et al. |
| 9,086,687 B2 | 7/2015 | Park et al. |
| D736,664 S | 8/2015 | Paradise et al. |
| 9,146,730 B2 | 9/2015 | Lazar |
| D741,855 S | 10/2015 | Park et al. |
| D742,272 S | 11/2015 | Bailey et al. |
| D742,874 S | 11/2015 | Cheng et al. |
| D743,963 S | 11/2015 | Osterhout |
| D747,714 S | 1/2016 | Erbeus |
| D750,623 S | 3/2016 | Park et al. |
| D751,065 S | 3/2016 | Magi |
| 9,299,248 B2 | 3/2016 | Lake et al. |
| D756,359 S | 5/2016 | Bailey et al. |
| 9,367,139 B2 | 6/2016 | Ataee et al. |
| 9,372,535 B2 | 6/2016 | Bailey et al. |
| 9,408,316 B2 * | 8/2016 | Bailey .................. A61B 5/681 |
| 9,418,927 B2 | 8/2016 | Axisa et al. |
| 9,472,956 B2 | 10/2016 | Michaelis et al. |
| 9,477,313 B2 * | 10/2016 | Mistry ................. G06F 3/04883 |
| 9,529,434 B2 | 12/2016 | Choi et al. |
| 9,600,030 B2 * | 3/2017 | Bailey .................... G06F 1/163 |
| 2002/0032386 A1 | 3/2002 | Sackner et al. |
| 2002/0077534 A1 | 6/2002 | DuRousseau |
| 2003/0030595 A1 * | 2/2003 | Radley-Smith ....... A44C 5/0007 345/1.3 |
| 2003/0036691 A1 | 2/2003 | Stanaland et al. |
| 2003/0051505 A1 * | 3/2003 | Robertson ............ A44C 11/002 63/3.2 |
| 2003/0144586 A1 | 7/2003 | Tsubata |
| 2004/0068409 A1 | 4/2004 | Tanaka et al. |
| 2004/0073104 A1 | 4/2004 | Brun del Re et al. |
| 2004/0194500 A1 | 10/2004 | Rapport |
| 2004/0210165 A1 | 10/2004 | Marmaropoulos et al. |
| 2005/0005637 A1 | 1/2005 | Rapport |
| 2005/0012715 A1 | 1/2005 | Ford |
| 2005/0070227 A1 | 3/2005 | Shen et al. |
| 2005/0119701 A1 | 6/2005 | Lauter et al. |
| 2005/0177038 A1 | 8/2005 | Kolpin et al. |
| 2006/0037359 A1 | 2/2006 | Spring |
| 2006/0061544 A1 | 3/2006 | Min et al. |
| 2007/0132785 A1 | 6/2007 | Ebersole, Jr. et al. |
| 2008/0136775 A1 | 6/2008 | Conant |
| 2009/0007597 A1 | 1/2009 | Hanevold |
| 2009/0031757 A1 | 2/2009 | Harding |
| 2009/0040016 A1 | 2/2009 | Ikeda |
| 2009/0051544 A1 | 2/2009 | Niknejad |
| 2009/0102580 A1 | 4/2009 | Uchaykin |
| 2009/0189867 A1 | 7/2009 | Krah et al. |
| 2009/0251407 A1 | 10/2009 | Flake et al. |
| 2009/0318785 A1 | 12/2009 | Ishikawa et al. |
| 2009/0326406 A1 | 12/2009 | Tan et al. |

(56) References Cited

U.S. PATENT DOCUMENTS

| | | |
|---|---|---|
| 2009/0327171 A1 | 12/2009 | Tan et al. |
| 2010/0041974 A1 | 2/2010 | Ting et al. |
| 2010/0280628 A1 | 11/2010 | Sankai |
| 2010/0293115 A1 | 11/2010 | Seyed Momen |
| 2010/0317958 A1 | 12/2010 | Beck et al. |
| 2011/0018754 A1 | 1/2011 | Tojima et al. |
| 2011/0065319 A1* | 3/2011 | Oster ............... H01R 13/2414 439/586 |
| 2011/0134026 A1 | 6/2011 | Kang et al. |
| 2011/0166434 A1 | 7/2011 | Gargiulo |
| 2011/0172503 A1 | 7/2011 | Knepper et al. |
| 2011/0213278 A1* | 9/2011 | Horak ................... A61B 5/112 600/595 |
| 2011/0224507 A1* | 9/2011 | Banet ..................... A61B 5/00 600/301 |
| 2011/0224556 A1* | 9/2011 | Moon ..................... A61B 5/00 600/485 |
| 2011/0224564 A1* | 9/2011 | Moon ..................... A61B 5/00 600/509 |
| 2012/0029322 A1 | 2/2012 | Wartena et al. |
| 2012/0051005 A1 | 3/2012 | Vanfleteren et al. |
| 2012/0052268 A1* | 3/2012 | Axisa ............... H01L 23/49838 428/212 |
| 2012/0101357 A1 | 4/2012 | Hoskuldsson et al. |
| 2012/0157789 A1 | 6/2012 | Kangas et al. |
| 2012/0165695 A1 | 6/2012 | Kidmose et al. |
| 2012/0188158 A1 | 7/2012 | Tan et al. |
| 2012/0203076 A1 | 8/2012 | Fatta et al. |
| 2012/0209134 A1 | 8/2012 | Morita et al. |
| 2012/0265090 A1 | 10/2012 | Fink et al. |
| 2012/0293548 A1 | 11/2012 | Perez et al. |
| 2012/0302858 A1 | 11/2012 | Kidmose et al. |
| 2012/0320532 A1* | 12/2012 | Wang ..................... H05K 1/189 361/720 |
| 2012/0323521 A1 | 12/2012 | De Foras et al. |
| 2013/0005303 A1 | 1/2013 | Song et al. |
| 2013/0020948 A1 | 1/2013 | Han et al. |
| 2013/0027341 A1 | 1/2013 | Mastandrea |
| 2013/0080794 A1* | 3/2013 | Hsieh ..................... G06F 1/26 713/300 |
| 2013/0123666 A1* | 5/2013 | Giuffrida ............. A61B 5/0024 600/595 |
| 2013/0127708 A1 | 5/2013 | Jung et al. |
| 2013/0165813 A1 | 6/2013 | Chang et al. |
| 2013/0191741 A1 | 7/2013 | Dickinson et al. |
| 2013/0198694 A1 | 8/2013 | Rahman et al. |
| 2013/0265229 A1 | 10/2013 | Forutanpour et al. |
| 2013/0265437 A1 | 10/2013 | Thom et al. |
| 2013/0271292 A1 | 10/2013 | McDermott |
| 2013/0312256 A1 | 11/2013 | Wesselmann et al. |
| 2013/0317648 A1 | 11/2013 | Assad |
| 2013/0332196 A1 | 12/2013 | Pinsker |
| 2014/0005743 A1* | 1/2014 | Giuffrida ............ A61N 1/36135 607/45 |
| 2014/0020945 A1 | 1/2014 | Hurwitz et al. |
| 2014/0028546 A1 | 1/2014 | Jeon et al. |
| 2014/0045547 A1 | 2/2014 | Singamsetty et al. |
| 2014/0049417 A1 | 2/2014 | Abdurrahman et al. |
| 2014/0051946 A1* | 2/2014 | Arne ..................... A61B 5/0022 600/301 |
| 2014/0074179 A1* | 3/2014 | Heldman ............. A61B 5/1101 607/45 |
| 2014/0094675 A1* | 4/2014 | Luna ................... A61B 5/02438 600/386 |
| 2014/0121471 A1* | 5/2014 | Walker ................. A61B 5/1128 600/301 |
| 2014/0122958 A1* | 5/2014 | Greenebrg ............. A61B 5/002 714/748 |
| 2014/0194062 A1 | 7/2014 | Palin et al. |
| 2014/0198034 A1 | 7/2014 | Bailey et al. |
| 2014/0198035 A1 | 7/2014 | Bailey et al. |
| 2014/0236031 A1 | 8/2014 | Banet et al. |
| 2014/0240103 A1 | 8/2014 | Lake et al. |
| 2014/0240223 A1* | 8/2014 | Lake ..................... G08C 17/02 345/156 |
| 2014/0249397 A1 | 9/2014 | Lake et al. |
| 2014/0257141 A1* | 9/2014 | Giuffrida ............. A61B 5/1124 600/595 |
| 2014/0285326 A1* | 9/2014 | Luna ................... F21V 33/0056 340/12.3 |
| 2014/0299362 A1 | 10/2014 | Park et al. |
| 2014/0334083 A1 | 11/2014 | Bailey |
| 2014/0334653 A1* | 11/2014 | Luna ..................... G05B 15/02 381/332 |
| 2014/0337861 A1 | 11/2014 | Chang et al. |
| 2014/0340857 A1 | 11/2014 | Hsu et al. |
| 2014/0349257 A1 | 11/2014 | Connor |
| 2014/0375465 A1 | 11/2014 | Fenuccio et al. |
| 2014/0354528 A1 | 12/2014 | Laughlin et al. |
| 2014/0354529 A1 | 12/2014 | Laughlin et al. |
| 2014/0364703 A1 | 12/2014 | Kim et al. |
| 2014/0368424 A1* | 12/2014 | Choi ..................... G06F 3/015 345/156 |
| 2015/0011857 A1 | 1/2015 | Henson et al. |
| 2015/0025355 A1 | 1/2015 | Bailey et al. |
| 2015/0057506 A1* | 2/2015 | Luna ................... A61B 5/02438 600/301 |
| 2015/0057770 A1 | 2/2015 | Bailey et al. |
| 2015/0065840 A1 | 3/2015 | Bailey |
| 2015/0084860 A1 | 3/2015 | Aleem et al. |
| 2015/0106052 A1* | 4/2015 | Balakrishnan ......... A61B 5/7246 702/150 |
| 2015/0109202 A1 | 4/2015 | Ataee et al. |
| 2015/0124566 A1 | 5/2015 | Lake et al. |
| 2015/0141784 A1 | 5/2015 | Morun et al. |
| 2015/0148641 A1 | 5/2015 | Morun et al. |
| 2015/0160621 A1 | 6/2015 | Yilmaz |
| 2015/0182113 A1* | 7/2015 | Utter, II ............... A61B 5/0022 340/539.12 |
| 2015/0182130 A1* | 7/2015 | Utter, II ............... A61B 5/0205 600/483 |
| 2015/0182163 A1* | 7/2015 | Utter ................... A61B 5/0022 600/301 |
| 2015/0182164 A1* | 7/2015 | Utter, II ............... A61B 5/0022 600/301 |
| 2015/0186609 A1* | 7/2015 | Utter, II ............... A61B 5/0022 600/301 |
| 2015/0216475 A1* | 8/2015 | Luna ................... A61B 5/02438 600/301 |
| 2015/0230756 A1* | 8/2015 | Luna ..................... A61B 5/721 600/484 |
| 2015/0234426 A1 | 8/2015 | Bailey et al. |
| 2015/0237716 A1 | 8/2015 | Su et al. |
| 2015/0261306 A1 | 9/2015 | Lake |
| 2015/0277575 A1 | 10/2015 | Ataee et al. |
| 2015/0296553 A1 | 10/2015 | DiFranco et al. |
| 2015/0325202 A1 | 11/2015 | Lake et al. |
| 2015/0370333 A1 | 12/2015 | Ataee et al. |
| 2016/0020500 A1 | 1/2016 | Matsuda |
| 2016/0150636 A1 | 5/2016 | Otsubo |
| 2016/0156762 A1 | 6/2016 | Bailey et al. |
| 2016/0199699 A1 | 7/2016 | Klassen |
| 2016/0202081 A1 | 7/2016 | Debieuvre et al. |
| 2016/0274758 A1 | 9/2016 | Bailey |
| 2016/0309249 A1 | 10/2016 | Wu et al. |
| 2016/0313899 A1 | 10/2016 | Noel |

FOREIGN PATENT DOCUMENTS

| | | |
|---|---|---|
| JP | 2009-50679 A | 3/2009 |
| KR | 20120094870 A | 8/2012 |
| KR | 20120097997 A | 9/2012 |
| WO | 2011/070554 A2 | 6/2011 |

OTHER PUBLICATIONS

Communication pursuant to Rule 164(1) EPC, dated Sep. 30, 2016, for corresponding EP Application No. 14753949.8, 7 pages.

(56) References Cited

OTHER PUBLICATIONS

Costanza et al., "EMG as a Subtle Input Interface for Mobile Computing," Mobile HCI 2004, LNCS 3160, edited by S. Brewster and M. Dunlop, Springer-Verlag Berlin Heidelberg, pp. 426-430, 2004.
Costanza et al., "Toward Subtle Intimate Interfaces for Mobile Devices Using an EMG Controller," CHI 2005, Proceedings of the SIGCHI Conference on Human Factors in Computing Systems, pp. 481-489, 2005.
Ghasemzadeh et al., "A Body Sensor Network With Electromyogram and Inertial Sensors: Multimodal Interpretation of Muscular Activities," IEEE Transactions on Information Technology in Biomedicine, vol. 14, No. 2, pp. 198-206, Mar. 2010.
Gourmelon et al., "Contactless sensors for Surface Electromyography," Proceedings of the 28th IEEE EMBS Annual International Conference, New York City, NY, Aug. 30-Sep. 3, 2006, pp. 2514-2517.
International Search Report and Written Opinion, dated May 16, 2014, for corresponding International Application No. PCT/US2014/017799, 9 pages.
International Search Report and Written Opinion, dated Aug. 21, 2014, for corresponding International Application No. PCT/US2014/037863, 10 pages.
International Search Report and Written Opinion, dated Nov. 21, 2014, for corresponding International Application No. PCT/US2014/052143, 9 pages.
International Search Report and Written Opinion, dated Feb. 27, 2015, for corresponding International Application No. PCT/US2014/067443, 10 pages.
International Search Report and Written Opinion, dated May 27, 2015, for corresponding International Application No. PCT/US2015/015675, 9 pages.
Morris et al., "Emerging Input Technologies for Always-Available Mobile Interaction," *Foundations and Trends in Human-Computer Interaction* 4(4):245-316, 2010. (74 total pages).
Naik et al., "Real-Time Hand Gesture Identification for Human Computer Interaction Based on ICA of Surface Electromyogram," IADIS International Conference Interfaces and Human Computer Interaction 2007, 8 pages.
Picard et al., "Affective Wearables," Proceedings of the IEEE $1^{st}$ International Symposium on Wearable Computers, ISWC, Cambridge, MA, USA, Oct. 13-14, 1997, pp. 90-97.
Rekimoto, "GestureWrist and GesturePad: Unobtrusive Wearable Interaction Devices," ISWC '01 Proceedings of the $5^{th}$ IEEE International Symposium on Wearable Computers, 2001, 7 pages.
Saponas et al., "Making Muscle-Computer Interfaces More Practical," CHI 2010, Atlanta, Georgia, USA, Apr. 10-15, 2010, 4 pages.
Sato et al., "Touche: Enhancing Touch Interaction on Humans, Screens, Liquids, and Everyday Objects," CHI' 12, May 5-10, 2012, Austin, Texas.
Ueno et al., "A Capacitive Sensor System for Measuring Laplacian Electromyogram through Cloth: A Pilot Study," Proceedings of the $29^{th}$ Annual International Conference of the IEEE EMBS, Cite Internationale, Lyon, France, Aug. 23-26, 2007.
Ueno et al., "Feasibility of Capacitive Sensing of Surface Electromyographic Potential through Cloth," *Sensors and Materials* 24(6):335-346, 2012.
Xiong et al., "A Novel HCI based on EMG and IMU," Proceedings of the 2011 IEEE International Conference on Robotics and Biomimetics, Phuket, Thailand, Dec. 7-11, 2011, 5 pages.
Zhang et al., "A Framework for Hand Gesture Recognition Based on Accelerometer and EMG Sensors," IEEE Transactions on Systems, Man, and Cybernetics—Part A: Systems and Humans, vol. 41, No. 6, pp. 1064-1076, Nov. 2011.
Xu et al., "Hand Gesture Recognition and Virtual Game Control Based on 3D Accelerometer and EMG Sensors," Proceedings of the 14th international conference on Intelligent user interfaces, Sanibel Island, Florida, Feb. 8-11, 2009, pp. 401-406.

\* cited by examiner

SYSTEMS, ARTICLES AND METHODS FOR SIGNAL ROUTING IN WEARABLE ELECTRONIC DEVICES THAT DETECT MUSCLE ACTIVITY OF A USER USING A SET OF DISCRETE AND SEPARATELY ENCLOSED POD STRUCTURES

BACKGROUND

Technical Field

The present systems, articles and methods generally relate to wearable electronic devices and particularly relate to systems, articles and methods for signal routing in wearable electronic devices.

Description of the Related Art

Wearable Electronic Devices

Electronic devices are commonplace throughout most of the world today. Advancements in integrated circuit technology have enabled the development of electronic devices that are sufficiently small and lightweight to be carried by the user. Such "portable" electronic devices may include on-board power supplies (such as batteries or other power storage systems) and may be designed to operate without any wire-connections to other electronic systems; however, a small and lightweight electronic device may still be considered portable even if it includes a wire-connection to another electronic system. For example, a microphone may be considered a portable electronic device whether it is operated wirelessly or through a wire-connection.

The convenience afforded by the portability of electronic devices has fostered a huge industry. Smartphones, audio players, laptop computers, tablet computers, and ebook readers are all examples of portable electronic devices. However, the convenience of being able to carry a portable electronic device has also introduced the inconvenience of having one's hand(s) encumbered by the device itself. This problem is addressed by making an electronic device not only portable, but wearable.

A wearable electronic device is any portable electronic device that a user can carry without physically grasping, clutching, or otherwise holding onto the device with their hands. For example, a wearable electronic device may be attached or coupled to the user by a strap or straps, a band or bands, a clip or clips, an adhesive, a pin and clasp, an article of clothing, tension or elastic support, an interference fit, an ergonomic form, etc. Examples of wearable electronic devices include digital wristwatches, electronic armbands, electronic rings, electronic ankle-bracelets or "anklets," head-mounted electronic display units, hearing aids, and so on.

Two exemplary design factors for wearable electronic devices that may be of importance to users are: functionality and affordability. The functionality of a wearable electronic device is, of course, dependent on the electric circuitry (i.e., the electrical/electronic components and the electrical wiring therebetween) that the device employs. Users of wearable electronic devices may desire more sophisticated functionality, but more sophisticated functionality may adversely affect affordability. Affordability is directly tied to manufacturability, and more sophisticated functionality may necessitate more expensive electric circuitry or manufacturing processes that drive up manufacturing costs. There is a need in the art for wearable electronic device designs that provide desired functionality without compromising affordability.

Human-Electronics Interfaces

A wearable electronic device may provide direct functionality for a user (such as audio playback, data display, computing functions, etc.) or it may provide electronics to interact with, receive information from, or control another electronic device. For example, a wearable electronic device may include sensors that detect inputs effected by a user and transmit signals to another electronic device based on those inputs. Sensor-types and input-types may each take on a variety of forms, including but not limited to: tactile sensors (e.g., buttons, switches, touchpads, or keys) providing manual control, acoustic sensors providing voice-control, electromyography sensors providing gesture control, and/or accelerometers providing gesture control.

A human-computer interface ("HCI") is an example of a human-electronics interface. The present systems, articles, and methods may be applied to wearable HCIs, but may also be applied to any other form of wearable human-electronics interface.

BRIEF SUMMARY

A wearable electronic device may be summarized as including a set of pod structures that form physically coupled links of the wearable electronic device, wherein each pod structure in the set of pod structures is positioned adjacent and physically coupled to at least one other pod structure in the set of pod structures, and wherein the set of pod structures comprises at least two sensor pods and a processor pod, each of the at least two sensor pods comprising a respective sensor to in use detect inputs effected by a user and provide signals in response to the detected inputs, and the processor pod comprising a processor to in use process signals provided by each of the at least two sensor pods; and a plurality of communicative pathways to in use route signals provided by the at least two sensor pods to the processor pod, wherein each of the at least two sensor pods is communicatively coupled to the processor pod by at least one respective communicative pathway from the plurality of communicative pathways. Each of the at least two sensor pods may include a respective amplification circuit to in use amplify signals provided by the respective sensor.

The processor pod may include at least one analog-to-digital conversion ("ADC") circuit to in use convert analog signals provided by the at least two sensor pods into digital signals. The at least two sensor pods may include a first sensor pod and a second sensor pod, the first sensor pod communicatively coupled to the processor pod by a first communicative pathway from the plurality of communicative pathways and the second sensor pod communicatively coupled to the processor pod by a second communicative pathway from the plurality of communicative pathways, and: the first communicative pathway may include: a first portion to in use route analog signals output by the first sensor pod to the processor pod, and the second communicative pathway may include: a first portion to in use route analog signals output by the second sensor pod to the first sensor pod, and a second portion to in use route analog signals output by the second sensor pod from the first sensor pod to the processor pod. The at least two sensor pods may further include a third sensor pod, the third sensor pod communicatively coupled to the processor pod by a third communicative pathway from the plurality of communicative pathways, and the third communicative pathway may include: a first portion to in use route analog signals output by the third sensor pod to the second sensor pod; a second portion to in use route analog signals output by the third sensor pod from the second sensor pod to the first sensor pod; and a third portion to in use route analog signals output by the third sensor pod from the first sensor pod to the processor pod. The at least two sensor pods may further include a fourth sensor pod, the fourth sensor pod communicatively coupled to the processor pod by a fourth communicative pathway from the plurality of communicative pathways, and the fourth communicative pathway may include: a first portion to in use route analog signals output by the fourth sensor pod to the third sensor pod; a second portion to in use route analog signals output by the fourth sensor pod from the third sensor pod to the second sensor pod; a third portion to in use route analog signals output by the fourth sensor pod from the second sensor pod to the first sensor pod; and a fourth portion to in use route analog signals output by the fourth sensor pod from the first sensor pod to the processor pod.

Each of the at least two sensor pods may include a respective analog-to-digital conversion ("ADC") circuit to in use convert analog signals provided by the respective sensor into digital signals. The wearable electronic device may further include a clock signal line communicatively coupled to each pod structure in the set of pod structures and wherein the plurality of communicative pathways includes a digital signal bus that is communicatively coupled to the processor pod, wherein the at least two sensor pods include a first sensor pod and a second sensor pod, the first sensor pod communicatively coupled to the digital signal bus by a first communicative pathway from the plurality of communicative pathways and the second sensor pod communicatively coupled to the digital signal bus by a second communicative pathway from the plurality of communicative pathways. The at least two sensor pods may further include a third sensor pod, the third sensor pod communicatively coupled to the digital signal bus by a third communicative pathway from the plurality of communicative pathways. The at least two sensor pods may further include a fourth sensor pod, the fourth sensor pod communicatively coupled to the digital signal bus by a fourth communicative pathway from the plurality of communicative pathways.

The plurality of communicative pathways may include at least one power line and at least one ground line.

The wearable electronic device may further include at least one adaptive coupler, wherein each respective pod structure in the set of pod structures is adaptively physically coupled to at least one adjacent pod structure in the set of pod structures by at least one adaptive coupler. For each of the at least two sensor pods, the sensor may include an electromyography sensor to in use detect muscle activity by the user and provide signals in response to the detected muscle activity.

The processor pod may further include: a sensor to in use detect inputs effected by the user and provide analog signals in response to the detected inputs; an amplification circuit to in use amplify analog signals provided by the sensor; and an analog-to-digital conversion ("ADC") circuit to in use convert analog signals into digital signals. Each pod structure in the set of pod structures may include a respective housing formed of a substantially rigid material and having a respective inner volume, and, for each of the at least two sensor pods, the sensor may be positioned on or proximate a surface of the housing, while for the processor pod, the processor may be positioned in the inner volume of the housing, and each communicative pathway in the plurality of communicative pathways may include a respective first portion in the inner volume of the housing of a respective first pod structure in the set of pod structures, a respective second portion in the inner volume of the housing of a respective second pod structure in the set of pod structures, and a respective third portion that extends between the housing of the respective first pod structure in the set of pod structures and the housing of the respective second pod structure in the set of pod structures.

At least one communicative pathway in the plurality of communicative pathways may be selected from the group consisting of: an electrically conductive pathway and an optical pathway. At least one communicative pathway in the plurality of communicative pathways may comprise or be a component of a flexible printed circuit board. Each pod structure in the set of pod structures may be positioned adjacent and in between two other pod structures in the set of pod structures and physically coupled to the two other pod structures in the set of pod structures, and the set of pod structures may form a perimeter of an annular configuration.

A wearable electronic device may be summarized as including: a set of pod structures that form physically coupled links of the wearable electronic device, the set of pod structures comprising a plurality of sensor pods and a processor pod, each sensor pod comprising a respective sensor to in use detect inputs effected by a user and provide signals in response to the detected inputs, and the processor pod comprising a processor to in use process signals provided by the plurality of sensor pods, wherein each pod structure in the set of pod structures is positioned adjacent and physically coupled to at least one other pod structure in the set of pod structures; and a plurality of communicative pathways to in use route signals provided by the plurality of sensor pods to the processor pod, wherein each pod structure in the set of pod structures is communicatively coupled to at least one adjacent pod structure in the set of pod structures by a respective communicative pathway from the plurality of communicative pathways to in use serially route signals provided by each sensor pod to the processor pod via successive ones of adjacent pod structures in the set of pod structures by respective communicative pathways in the plurality of communicative pathways.

The plurality of sensor pods may include: a first sensor pod positioned adjacent and physically coupled to the processor pod; a second sensor pod positioned adjacent and physically coupled to the processor pod; a third sensor pod positioned adjacent and physically coupled to the first sensor pod; and a fourth sensor pod positioned adjacent and physically coupled to the second sensor pod. The first sensor pod may be communicatively coupled to the processor pod by a first communicative pathway in the plurality of communicative pathways to in use route signals provided by the first sensor pod to the processor pod. The second sensor pod may be communicatively coupled to the processor pod by a second communicative pathway in the plurality of communicative pathways to in use route signals provided by the second sensor pod to the processor pod. The third sensor pod may be communicatively coupled to the processor pod by a third communicative pathway in the plurality of communicative pathways to in use route signals output by the third sensor pod from the third sensor pod via the first sensor pod to the processor pod. The fourth sensor pod may be communicatively coupled to the processor pod by a fourth communicative pathway in the plurality of communicative pathways to in use route signals output by the fourth sensor pod from the fourth sensor pod via the second sensor pod to the processor pod. The third communicative pathway may include at least a portion of the first communicative pathway and the fourth communicative pathway may include at least a portion of the second communicative pathway.

The processor pod may further include an analog-to-digital conversion ("ADC") circuit to in use convert analog signals into digital signals. Each sensor pod in the plurality of sensor pods may include a respective analog-to-digital conversion ("ADC") circuit to in use convert analog signals into digital signals. The plurality of communicative pathways may include at least one power line and at least one ground line.

The wearable electronic device may further include: at least one adaptive coupler, wherein each respective pod structure in the set of pod structures is adaptively physically coupled to at least one adjacent pod structure in the set of pod structures by at least one adaptive coupler. For each sensor pod in the plurality of sensor pods: the sensor may include an electromyography sensor to in use detect muscle activity by the user and provide signals in response to the detected muscle activity. The processor pod may include a sensor to in use detect inputs effected by the user and provide signals in response to the detected inputs.

Each pod structure in the set of pod structures may include a respective housing formed of a substantially rigid material and having a respective inner volume, and, for each sensor pod in the plurality of sensor pods, the sensor may be positioned on or proximate a surface of the housing, while for the processor pod, the processor may be positioned in the inner volume of the housing, and each communicative pathway in the plurality of communicative pathways may include a respective first portion in the inner volume of the housing of a respective first pod structure in the set of pod structures, a respective second portion in the inner volume of the housing of a respective second pod structure in the set of pod structures, and a respective third portion that extends between the housing of the respective first pod structure in the set of pod structures and the housing of the respective second pod structure in the set of pod structures.

At least one communicative pathway in the plurality of communicative pathways may be selected from the group consisting of: an electrically conductive pathway and an optical pathway. At least one communicative pathway in the plurality of communicative pathways may include or be a component of a flexible printed circuit board. Each pod structure in the set of pod structures may be positioned adjacent and in between two other pod structures in the set of pod structures and physically coupled to the two other pod structures in the set of pod structures, and the set of pod structures may form a perimeter of an annular configuration.

A method of operating a wearable electronic device that comprises a set of pod structures and a plurality of communicative pathways, the set of pod structures including a plurality of sensor pods and a processor pod, wherein each sensor pod in the plurality of sensor pods comprises a respective sensor and the processor pod comprises a processor, and wherein each pod structure in the set of pod structures is positioned adjacent and physically coupled to at least one other pod structure in the set of pod structures, may be summarized as including: detecting inputs effected by a user by the sensor in at least one sensor pod in the plurality of sensor pods; providing signals in response to the detected inputs by the sensor in the at least one sensor pod in the plurality of sensor pods; serially routing the signals via successive ones of adjacent pod structures in the set of pod structures by respective communicative pathways in the plurality of communicative pathways until the signals are routed to the processor pod; and processing the signals by the processor in the processor pod.

Providing signals in response to the detected inputs by the sensor in the at least one sensor pod in the plurality of sensor pods may include providing analog signals in response to the detected inputs by the sensor in the at least one sensor pod in the plurality of sensor pods. Serially routing the signals via successive ones of adjacent pod structures in the set of pod structures by respective communicative pathways in the plurality of communicative pathways until the signals are routed to the processor pod may include serially routing the analog signals via successive ones of adjacent pod structures in the set of pod structures by respective communicative pathways in the plurality of communicative pathways until the analog signals are routed to the processor pod. The processor pod may include an analog-to-digital conversion ("ADC") circuit, and the method further include converting the analog signals into digital signals by the ADC circuit in the processor pod, wherein processing the signals by the processor in the processor pod includes processing the digital signals by the processor in the processor pod.

Providing signals in response to the detected inputs by the sensor in the at least one sensor pod in the plurality of sensor pods may include providing analog signals in response to the detected inputs by the sensor in the at least one sensor pod in the plurality of sensor pods, and each sensor pod in the plurality of sensor pods may include a respective analog-to-digital conversion ("ADC") circuit, with the method further including: converting the analog signals provided by the sensor in the at least one sensor pod in the plurality of sensor pods into digital signals by the ADC circuit in the at least one sensor pod in the plurality of sensor pods, wherein: serially routing the signals via successive ones of adjacent pod structures in the set of pod structures by respective communicative pathways in the plurality of communicative pathways until the signals are routed to the processor pod includes serially routing the digital signals via successive ones of adjacent pod structures in the set of pod structures by respective communicative pathways in the plurality of communicative pathways until the digital signals are routed to the processor pod, and processing the signals by the processor in the processor pod includes processing the digital signals by the processor in the processor pod.

The respective sensor in each sensor pod in the plurality of sensor pods may include an electromyography sensor, and detecting inputs effected by a user by the sensor in at least one sensor pod in the plurality of sensor pods may include detecting muscle activity of the user by the electromyography sensor in at least one sensor pod in the plurality of sensor pods and providing signals in response to the detected inputs by the sensor in the at least one sensor pod in the plurality of sensor pods may include providing signals in response to muscle activity of the user by the sensor in the at least one sensor pod in the plurality of sensor pods.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

Figure 1:
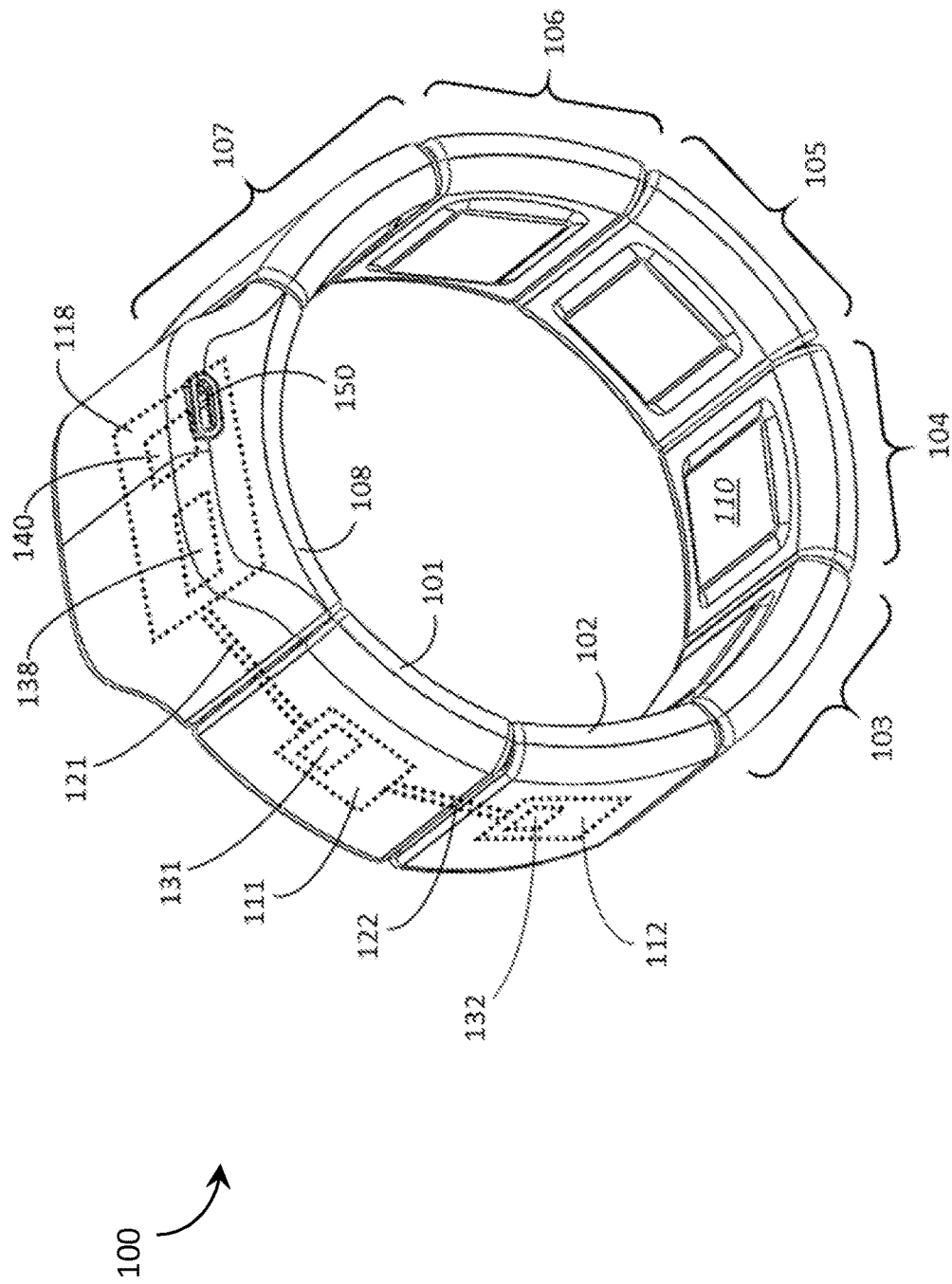
FIG. 1 is a perspective view of an exemplary wearable electronic device that employs signal routing techniques in accordance with the present systems, articles and methods.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electronic devices, and in particular portable electronic devices such as wearable electronic devices, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

The various embodiments described herein provide systems, articles, and methods for signal routing in wearable electronic devices. Throughout this specification and the appended claims, the term "routing" and its variants, such as "route," "routes," etc., refer to the guided transfer of a signal or signals (including but not limited to electrical signals and/or optical signals) from a first component to a second component, with or without passing over or through any number of intervening components. For example, a signal may be routed directly from component A to component B by one or more communicative pathway(s) that couple(s) component A to component B, or a signal may be routed indirectly from component A to component B via an intervening component C by one or more communicative pathway(s) having a first portion that couples component A to component C and a second portion that couples component C to component B.

Throughout this specification and the appended claims, the term "via" in the context of signal routing is generally used to indicate that a signal is routed, transmitted, or otherwise directed over or through an intervening point or structure en route from a first point or structure to a second point or structure. A signal may be routed from a first point A to a second point B "via" an intervening point C by physically and/or communicatively coupling to one or more component(s) at the intervening point C. For example, a signal may be routed from a first point A to a second point B via an intervening point C by a communicative pathway comprising a first electrically conductive trace that electrically communicatively couples a component at point A to a component at point C and a second electrically conductive trace that electrically communicatively couples the component at point C to a component at point B. However, a signal may also be routed from a first point A to a second point B via an intervening point C by a communicative pathway comprising a single electrically conductive trace that electrically communicatively couples a component at point A to a component at point B and physically extends over or through point C in between points A and B without electrically communicatively coupling to any component(s) at point C.

Throughout this specification and the appended claims, the term "signal" is generally used to refer to information in any format and in any type of tangible, non-transitory medium that stores, represents, or otherwise embodies information and carries that information when transmitted. Exemplary signals that may be employed by and/or that may employ the present systems, articles, and methods include, but are not limited to, electrical signals, magnetic signals and/or optical signals. Similarly, throughout this specification and the appended claims the term "communicative" as in "communicative pathway," "communicative coupling," and in variants such as "communicatively coupled," is generally used to refer to an engineered configuration for transferring and/or exchanging information. Exemplary communicative pathways include, but are not limited to, electrically conductive pathways (e.g., electrically conductive wires, electrically conductive traces), magnetic pathways (e.g., magnetic media), and/or optical pathways (e.g., optical fiber), and exemplary communicative couplings include, but are not limited to, electrical couplings and/or optical couplings. In general, a "communicative pathway" may include any number of serially-linked portions through which a signal is routed.

As previously described, there are at least two exemplary design factors for a wearable electronic device that influence signal routing: functionality and affordability/manufacturability. These two factors (and potentially many others) may be of great interest to potential users of wearable electronic devices, but they may each be influenced in different ways by signal routing design choices. A typical user may desire sophisticated functionality at minimal cost. The present systems, articles, and methods describe wearable electronic devices that employ signal routing techniques that achieve desired functionality without compromising manufacturability.

FIG. 1 is a perspective view of an exemplary wearable electronic device 100 that employs signal routing techniques in accordance with the present systems, articles and methods. Exemplary device 100 is an armband designed to be worn on the wrist, forearm, or upper arm of a user, though a person of skill in the art will appreciate that the teachings described herein may readily be applied in wearable electronic devices designed to be worn elsewhere on the body of the user (such as on a finger, leg, ankle, neck, or torso of the user). Device 100 includes a set of eight pod structures 101, 102, 103, 104, 105, 106, 107, and 108 that form physically coupled links of the wearable electronic device 100. Each pod structure in the set of eight pod structures 101, 102, 103, 104, 105, 106, 107, and 108 is positioned adjacent and in between two other pod structures in the set of eight pod structures and the set of pod structures forms a perimeter of an annular or closed loop configuration. For example, pod structure 101 is positioned adjacent and in between pod structures 102 and 108 at least approximately on a perimeter of the annular or closed loop configuration of pod structures, pod structure 102 is positioned adjacent and in between pod structures 101 and 103 at least approximately on the perimeter of the annular or closed loop configuration, pod structure 103 is positioned adjacent and in between pod structures 102 and 104 at least approximately on the perimeter of the annular or closed loop configuration, and so on. Each of pod structures 101, 102, 103, 104, 105, 106, 107, and 108 is physically coupled to the two adjacent pod structures by at least one adaptive coupler (not shown in FIG. 1). For example, pod structure 101 is physically coupled to pod structure 108 by an adaptive coupler and to pod structure 102 by an adaptive coupler. The term "adaptive coupler" is used throughout this specification and the appended claims to denote a system, article or device that provides flexible, adjustable, modifiable, extendable, extensible, or otherwise "adaptive" physical coupling. Adaptive coupling is physical coupling between two objects that permits limited motion of the two objects relative to one another. An example of an adaptive coupler is an elastic material such as an elastic band. Thus, each of pod structures 101, 102, 103, 104, 105, 106, 107, and 108 in the set of eight pod structures may be adaptively physically coupled to the two adjacent pod structures by at least one elastic band. The set of eight pod structures may be physically bound in the annular or closed loop configuration by a single elastic band that couples over or through all pod structures or by multiple separate elastic bands that couple between adjacent pairs of pod structures or between groups of adjacent pairs of pod structures. Device 100 is depicted in FIG. 1 with the at least one adaptive coupler completely retracted and contained within the eight pod structures 101, 102, 103, 104, 105, 106, 107, and 108 (and therefore the at least one adaptive coupler is not visible in FIG. 1). Further details of adaptive coupling in wearable electronic devices are described in, for example, U.S. Provisional Application Ser. No. 61/860,063 (now U.S. Non-Provisional patent application Ser. No. 14/276,575), which is incorporated herein by reference in its entirety.

Throughout this specification and the appended claims, the term "pod structure" is used to refer to an individual link, segment, pod, section, structure, component, etc. of a wearable electronic device. For the purposes of the present systems, articles, and methods, an "individual link, segment, pod, section, structure, component, etc." (i.e., a "pod structure") of a wearable electronic device is characterized by its ability to be moved or displaced relative to another link, segment, pod, section, structure component, etc. of the wearable electronic device. For example, pod structures 101 and 102 of device 100 can each be moved or displaced relative to one another within the constraints imposed by the adaptive coupler providing adaptive physical coupling therebetween. The desire for pod structures 101 and 102 to be movable/displaceable relative to one another specifically arises because device 100 is a wearable electronic device that advantageously accommodates the movements of a user and/or different user forms.

Throughout this specification and the appended claims the term "physically coupled" is generally used to encompass both direct and indirect physical coupling. That is, in the present systems, articles, and methods, two objects are considered "physically coupled" if they are in direct physical contact with one another or if they are indirectly physically connected through one or more intervening structures, such as an adaptive coupler.

Device 100 includes eight pod structures 101, 102, 103, 104, 105, 106, 107, and 108 that form physically coupled links of the device 100. The number of pod structures included in a wearable electronic device is dependent on at least the nature, function(s), and design of the wearable electronic device, and the present systems, articles, and methods may be applied to any wearable electronic device employing any number of pod structures, including wearable electronic devices employing more than eight pod structures and wearable electronic devices employing fewer than eight pod structures.

In exemplary device 100 of FIG. 1, each of pod structures 101, 102, 103, 104, 105, 106, 107, and 108 comprises a respective housing having a respective inner volume. Each housing may be formed of substantially rigid material and may be optically opaque. Thus, details of the components contained within the housings (i.e., within the inner volumes of the housings) of pod structures 101, 102, 103, 104, 105, 106, 107, and 108 are not visible in FIG. 1. To facilitate descriptions of exemplary device 100, some internal components are depicted by dashed lines in FIG. 1 to indicate that these components are contained in the inner volume(s) of housings and not actually visible in the view depicted in FIG. 1 (unless an optically transparent or translucent housing material is used). For example, any or all of pod structures 101, 102, 103, 104, 105, 106, 107, and/or 108 may include electric circuitry. In FIG. 1, a first pod structure 101 is shown containing electric circuitry 111 (i.e., electric circuitry 111 is contained in the inner volume of the housing of pod structure 101), a second pod structure 102 is shown containing electric circuitry 112, and a third pod structure 108 is shown containing electric circuitry 118. The electric circuitry in any or all pod structures may be communicatively coupled to the electric circuitry in at least one other pod structure by at least one respective communicative pathway (e.g., by at least one electrically conductive pathway and/or by at least one optical pathway). For example, FIG. 1 shows a first communicative pathway 121 providing communicative coupling between electric circuitry 118 of pod structure 108 and electric circuitry 111 of pod structure 101, and a second communicative pathway 122 providing communicative coupling between electric circuitry 111 of pod structure 101 and electric circuitry 112 of pod structure 102. Communicative coupling between electric circuitries of pod structures in device 100 may include systems, articles, and methods for strain mitigation as described in U.S. Provisional Patent Application Ser. No. 61/857,105 (now U.S. Non-Provisional patent application Ser. No. 14/335,668), which is incorporated by reference herein in its entirety.

Throughout this specification and the appended claims, the term "rigid" as in, for example, "substantially rigid material," is used to describe a material that has an inherent tendency to maintain its shape and resist malformation/deformation under the moderate stresses and strains typically encountered by a wearable electronic device.

Each individual pod structure within a wearable electronic device may perform a particular function, or particular functions. For example, in device 100, each of pod structures 101, 102, 103, 104, 105, 106, and 107 includes a respective sensor 110 (only one called out in FIG. 1 to reduce clutter) to in use detect inputs effected by a user and to provide electrical signals in response to the detected inputs. Thus, each of pod structures 101, 102, 103, 104, 105, 106, and 107 may be referred to as a respective "sensor pod." Throughout this specification and the appended claims, the term "sensor pod" is used to denote an individual pod structure that includes at least one sensor or transducer to in use detect inputs effected by a user. Each sensor 110 may be any type of sensor that is capable of detecting any kind of signal produced, generated, or otherwise effected by the user, including but not limited to: an electromyography sensor, a magnetomyography sensor, a mechanomyography sensor, a blood pressure sensor, a heart rate sensor, a gyroscope, an accelerometer, a compass, and/or a thermometer. In exemplary device 100, each of sensor pods 101, 102, 103, 104, 105, 106, and 107 includes a respective electromyography sensor 110 (only one called out in FIG. 1 to reduce clutter) to in use detect inputs effected by the user in the form of electrical signals produced by muscle activity. Wearable electromyography device 100 may transmit information based on the detected muscle activity to provide a human-electronics interface (e.g., an HCI). Further details of exemplary wearable electromyography device 100 are described in U.S. Provisional Patent Application Ser. No. 61/752,226 (now U.S. Non-Provisional patent application Ser. No. 14/155,107), U.S. Provisional Patent Application Ser. No. 61/768,322 (now U.S. Non-Provisional patent application Ser. No. 14/186,889), and U.S. Provisional Patent Application Ser. No. 61/771,500 (now U.S. Non-Provisional patent application Ser. No. 14/194,252), each of which is incorporated herein by reference in its entirety. Those of skill in the art will appreciate, however, that a wearable electronic device having electromyography functionality is used only as an example in the present systems, articles, and methods and that the systems, articles and methods for signal routing in wearable electronic devices described herein are in no way limited to wearable electronic devices that employ electromyography sensors unless explicitly recited in a respective claim to such.

Pod structure 108 of device 100 includes a processor 140 that processes the signals provided by the sensors 110 of sensor pods 101, 102, 103 104, 105, 106, and 107 in response to user-effected input(s). Pod structure 108 may therefore be referred to as a "processor pod." Throughout this specification and the appended claims, the term "processor pod" is used to denote an individual pod structure that includes at least one processor to in use process signals. The processor may be any type of processor, including but not limited to: a digital microprocessor or microcontroller, an application-specific integrated circuit, a field-programmable gate array, or the like, that analyzes the signals to determine at least one output, action, or function based on the signals.

As used throughout this specification and the appended claims, the terms "sensor pod" and "processor pod" are not necessarily exclusive. A single pod structure may satisfy the definitions of both a "sensor pod" and a "processor pod" and may be referred to as either type of pod structure. For greater clarity, the term "sensor pod" is used to refer to any pod structure that includes a sensor and performs at least the function(s) of a sensor pod, and the term processor pod is used to refer to any pod structure that includes a processor and performs at least the function(s) of a processor pod. In device 100, processor pod 108 includes a sensor 110 (not visible in FIG. 1) to in use detect inputs effected by a user, so processor pod 108 could be referred to as a sensor pod. However, in exemplary device 100, processor pod 108 is the only pod structure that includes a processor 140, thus processor pod 108 is the only pod structure in exemplary device 100 that can be referred to as a processor pod. In alternative embodiments of device 100, multiple pod structures may include processors, and thus multiple pod structures may serve as processor pods. Similarly, some pod structures may not include sensors.

As previously described, each of pod structures 101, 102, 103, 104, 105, 106, 107, and 108 may include electric circuitry. FIG. 1 depicts electric circuitry 111 inside the inner volume of sensor pod 101, electric circuitry 112 inside the inner volume of sensor pod 102, and electric circuitry 118 inside the inner volume of processor pod 118. Circuitry 111 in sensor pod 101 includes at least component 131, circuitry 112 in sensor pod 102 includes at least component 132, and circuitry 118 in processor pod 108 includes at least components 138 and 140. The components and functions of the electric circuitry in any or all of pod structures 101, 102, 103, 104, 105, 106, 107, and/or 108 depend on the nature of device 100. As previously described, component 140 of circuitry 118 in processor pod 108 may include at least one processor (e.g., at least one microprocessor, digital signal processor (DSP), graphics processing unit (GPU), application specific integrated circuit (ASIC), programmable gate array (PGA) and/or programmable logic unit (PLU)). In the example of device 100 as an electromyography device, each of pod structures 101, 102, 103, 104, 105, 106, 107, and 108 may include a respective amplification circuit to in use amplify electrical signals provided by at least one respective sensor 110. For example, each of components 131, 132, and 138 may include a respective amplification circuit to in use amplify electrical signals provided by at least one respective sensor 110 in each of pod structures 101, 102, and 108. In this way, sensor pod 101 (and similarly sensor pod 102 and processor pod 108) may include an electromyography sensor 110 to provide analog signals in response to muscle activity by a user, and the sensor 110 of sensor pod 101 may be communicatively coupled to an amplification circuit 131 in electric circuitry 111 to amplify the analog signals provided by the sensor 110.

The electric circuitry of any or all of pod structures 101, 102, 103, 104, 105, 106, 107, and/or 108 may include an analog-to-digital conversion ("ADC") circuit to in use convert analog signals into digital signals. Thus, any or all of components 131, 132, and 138 may further include a respective ADC circuit to in use convert analog signals provided by at least one respective sensor 110 in each of pod structures 101, 102, and 108 into digital signals. In this way, sensor pod 101 (and similarly sensor pod 102 and processor pod 108) may include an electromyography sensor 110 to provide analog signals in response to muscle activity by a user, the sensor 110 of sensor pod 101 may be communicatively coupled to an amplification circuit 131 in electric circuitry 111 to amplify the analog signals provided by the sensor 110, and the amplification circuit 131 may be communicatively coupled to an ADC circuit 131 to convert the amplified analog signals into digital signals.

As will be described in more detail later, processor pod 108 may be the only one of pod structures 101, 102, 103, 104, 105, 106, 107, and 108 that includes an ADC circuit 138. In this configuration, amplified analog signals are routed through communicative pathways (e.g., communicative pathways 121 and 122) to processor pod 108. Alternatively, each of pod structures 101, 102, 103, 104, 105, 106, 107, and 108 may include a respective ADC circuit (e.g., 131, 132, and 138) and digital signals may be routed through communicative pathways (e.g., communicative pathways 121 and 122) to processor pod 108.

The electric circuitry (e.g., 111, 112, and/or 118) of any pod structure in device 100 may include other circuits, elements, or components, including but not limited to: filtering circuits, an optical signal generator to convert electrical signals into optical signals, an electrical signal generator to convert optical signals into electrical signals, a battery to provide a portable power source for device 100, a wireless transmitter (e.g., a Bluetooth® transmitter) to send signals to another electronic device based on the muscle activity signals detected by electromyography sensors 110, and/or a tethered connector port 150 (e.g., wired or optical) to provide a direct communicative coupling to another electronic device for the purpose of power transfer (e.g., recharging the battery) and/or data transfer. Connector port 150 is illustrated in FIG. 1 as a micro-Universal Serial Bus port, though a person of skill in the art will appreciate that any connector port may similarly be used, including but not limited to: a Universal Serial Bus port, a mini-Universal Serial Bus port, a SMA port, a THUNDERBOLT® port, and the like.

Signals that are provided by sensors 110 in device 100 are routed to processor pod 108 for processing by processor 140. The various embodiments described herein provide systems, articles, and methods to achieve this signal routing without comprising the manufacturability and/or affordability of device 100. To this end, device 100 employs a plurality of communicative pathways (e.g., 121 and 122) to route the signals that are provided by sensor pods 101, 102, 103, 104, 105, 106, and 107 to processor pod 108. Each respective pod structure 101, 102, 103, 104, 105, 106, 107, and 108 in device 100 is communicatively coupled to at least one other pod structure by at least one respective communicative pathway from the plurality of communicative pathways. Each communicative pathway (e.g., 121 and 122) may include any number of portions (e.g., a single continuous portion or multiple serially-linked portions) realized in any communicative form, including but not limited to: electrically conductive wires or cables, ribbon cables, fiber-optic cables, optical/photonic waveguides, electrically conductive traces carried by a rigid printed circuit board, and/or electrically conductive traces carried by a flexible printed circuit board.

Figure 2:
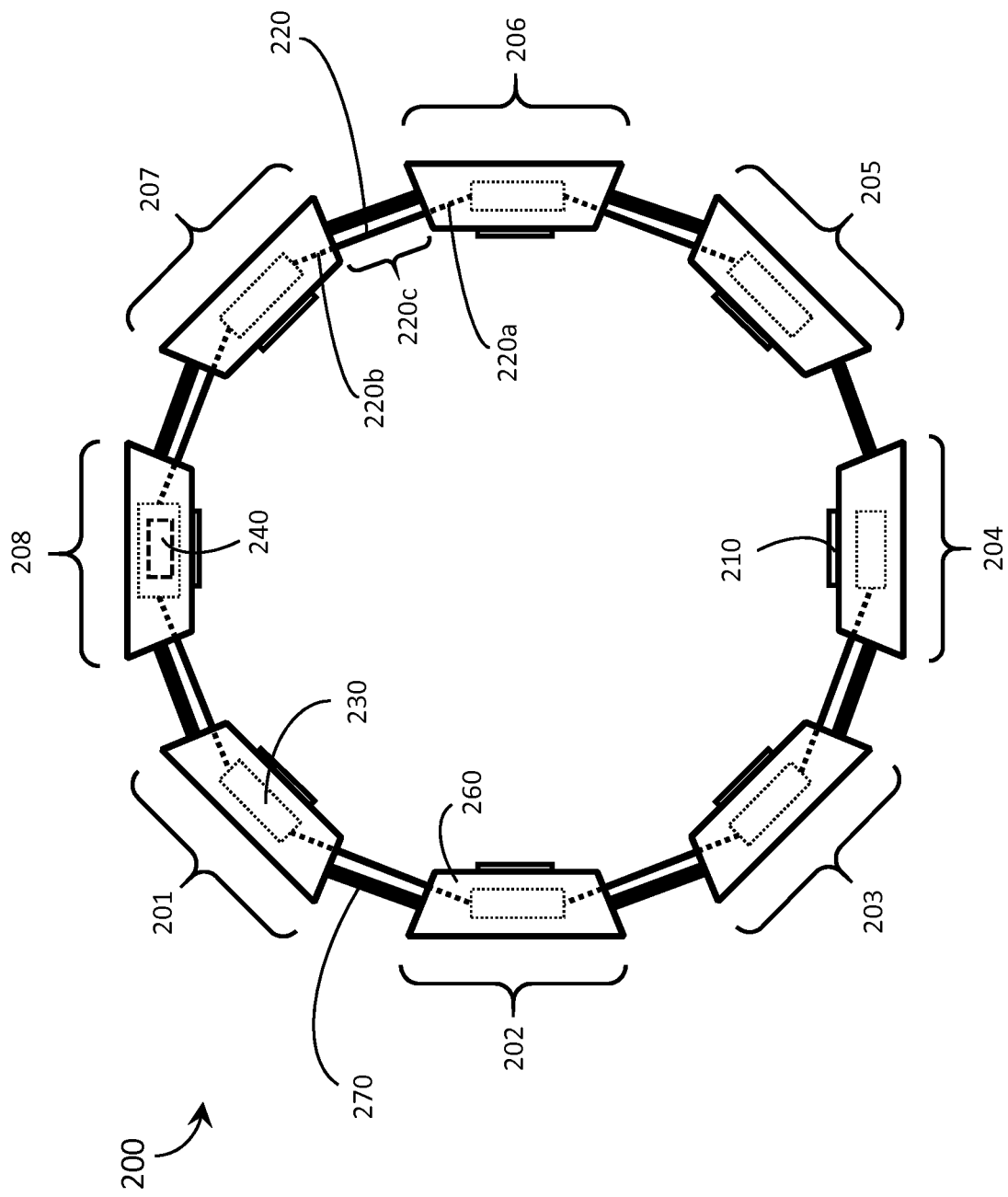
FIG. 2 is a side-elevation view of a wearable electronic device that employs signal routing in accordance with the present systems, articles, and methods.

FIG. 2 is a side-elevation view of a wearable electronic device 200 that employs signal routing in accordance with the present systems, articles, and methods. Device 200 is substantially similar to device 100 from FIG. 1 in that device 200 comprises a set of pod structures comprising sensor pods 201, 202, 203, 204, 205, 206, and 207 and processor pod 208 that form physically coupled links of wearable electronic device 200. Each pod structure is positioned adjacent at least one other pod structure (e.g., adjacent and in between two other pod structures) and the set of pod structures forms a perimeter of an annular or closed loop configuration. FIG. 2 shows device 200 in an expanded annular or closed loop configuration adapted to fit the arm of a larger user than the contracted annular or closed loop configuration of device 100 from FIG. 1. As a result, adaptive couplers 270 (only one called out in FIG. 2) providing adaptive physical coupling between adjacent pairs of pod structures are visible in FIG. 2, whereas such adaptive couplers 270 are not visible in FIG. 1. Each of sensor pods 201, 202, 203, 204, 205, 206, and 207 comprises a respective sensor 210 (only one called out in FIG. 2 to reduce clutter) to in use detect inputs effected by a user (e.g., an electromyography sensor to in use detect muscle activity by a user) and provide signals in response to the detected inputs. Processor pod 208 comprises a similar sensor 210 as well as a processor 240 that processes the signals provided by the respective sensors 210. Signals provided by sensors 210 are routed from each of sensor pods 201, 202, 203, 204, 205, 206, and 207 (in some cases via at least one adjacent sensor pod) to processor pod 208 by communicative pathways 220 (only one called out in FIG. 2 to reduce clutter).

Each of pod structures 201, 202, 203, 204, 205, 206, 207, and 208 comprises a respective housing 260 (only one called out in FIG. 2 to reduce clutter) formed of substantially rigid material and having an inner volume that contains at least a portion of respective electric circuitry 230 (only one called out in FIG. 2 to reduce clutter). Each of sensors 210 is positioned on or proximate a surface of a respective housing 260 and communicatively coupled to the electric circuitry 230 therein. For each of pod structures 201, 202, 203, 204, 205, 206, 207, and/or 208, electric circuitry 230 may include an amplification circuit and/or a filtering circuit and/or an ADC circuit. As previously described, housings 260 may be optically opaque, so some exemplary components within housings 260 (e.g., electrical circuitry 230) are illustrated with dashed lines to indicate that such components may not actually be visible in the view illustrated in FIG. 2. Each communicative pathway 220 provides communicative coupling between the respective electric circuitries 230 in each of two pod structures 201, 202, 203, 204, 205, 206, 207, and 208. Thus, each communicative pathway 220 includes a respective first portion 220a in the inner volume of the housing 260 of a respective first pod structure (e.g., sensor pod 206), a respective second portion 220b in the inner volume of the housing 260 of a respective second pod structure (e.g., sensor pod 207), and a respective third portion 220c that extends between the housing 260 of the respective first pod structure (e.g., sensor pod 206) and the housing 260 of the respective second pod structure (e.g., sensor pod 207).

FIG. 2 shows that communicative pathways 220 provide routes through which signals may be coupled from each of sensor pods 201, 202, 203, 204, 205, 206, and 207 to processor pod 208. Specifically, in accordance with the present systems, articles, and methods, the signals provided by each of sensor pods 201, 202, 203, 204, 205, 206, and 207 are serially routed via successive ones of adjacent pod structures in device 200 by communicative pathways 220 until the signals provided by each sensor pod 201, 202, 203, 204, 205, 206, 207 are routed to processor pod 208. For example, signals provided by a first sensor pod 201 are routed to processor pod 208 through a first communicative pathway 220 that communicatively couples first sensor pod 201 to processor pod 208; signals provided by a second sensor pod 202 are routed to processor pod 208 via first sensor pod 201 by a second communicative pathway 220 that communicatively couples the second sensor pod 202 to processor pod 208; signals provided by a third sensor pod 203 are routed to processor pod 208 via second sensor pod 202 and first sensor pod 201 by a third communicative pathway 220 that communicatively couples the third sensor pod 203 to processor pod 208; and signals provided by a fourth sensor pod 204 are routed to processor pod 208 via third sensor pod 203, second sensor pod 202, and first sensor pod 201 by a fourth communicative pathway 220 that communicatively couples the fourth sensor pod 204 to processor pod 208. Similar communicative pathways route signals from sensor pods 205, 206, and 207 to processor pod 208. Thus, signals from sensor pods 204, 203, 202, and 201 are routed "clockwise" around the annular configuration of device 200 (with respect to the view illustrated in FIG. 2) towards processor pod 208 and signals from sensor pods 205, 206, and 207 are routed "counter-clockwise" around the annular configuration of device 200 towards processor pod 208. The annular configuration of pod structures 201, 202, 203, 204, 205, 206, 207, and 208 allows a communicative "break" or "open" between one pair of adjacent pod structures. For example, device 200 does not include a communicative coupling between sensor pods 204 and 205 because signals from sensor pod 204 are routed to processor pod 208 by "clockwise" serial coupling between sensor pods 204, 203, 202, 201, and 208 while signals from sensor pod 205 are routed to processor pod 208 by "counter-clockwise" serial coupling between sensor pods 205, 206, 207, and 208, though a person of skill in the art will appreciate that, in alternative embodiments, a communicative coupling could be used to couple between sensor pods 204 and 205 and/or the communicative "break" or "open" may occur between any pair of adjacent pod structures in device 200.

As previously described, processor 240 in processor pod 208 may advantageously process digital signals. Analog signals may first be provided by sensors 210 in response to user-effected inputs, and any or all of electric circuitries 230 may include an ADC circuit that in use converts the analog signals into digital signals for processing by processor 240. When only the processor pod 208 includes an ADC circuit in its electric circuitry 230, each of sensor pods 201, 202, 203, 204, 205, 206, and 207 provides analog signals and analog signals are routed over/through/between the sensor pods to processor pod 208. When a respective ADC circuit is included in the electric circuitry 230 of each sensor pod 201, 202, 203, 204, 205, 206, and 207, then each sensor pod provides digital signals and digital signals are routed over/through/between the sensor pods to processor pod 208. The various embodiments described herein provide systems, articles, and methods for routing analog and/or digital signals within a wearable electronic device.

Figure 3:
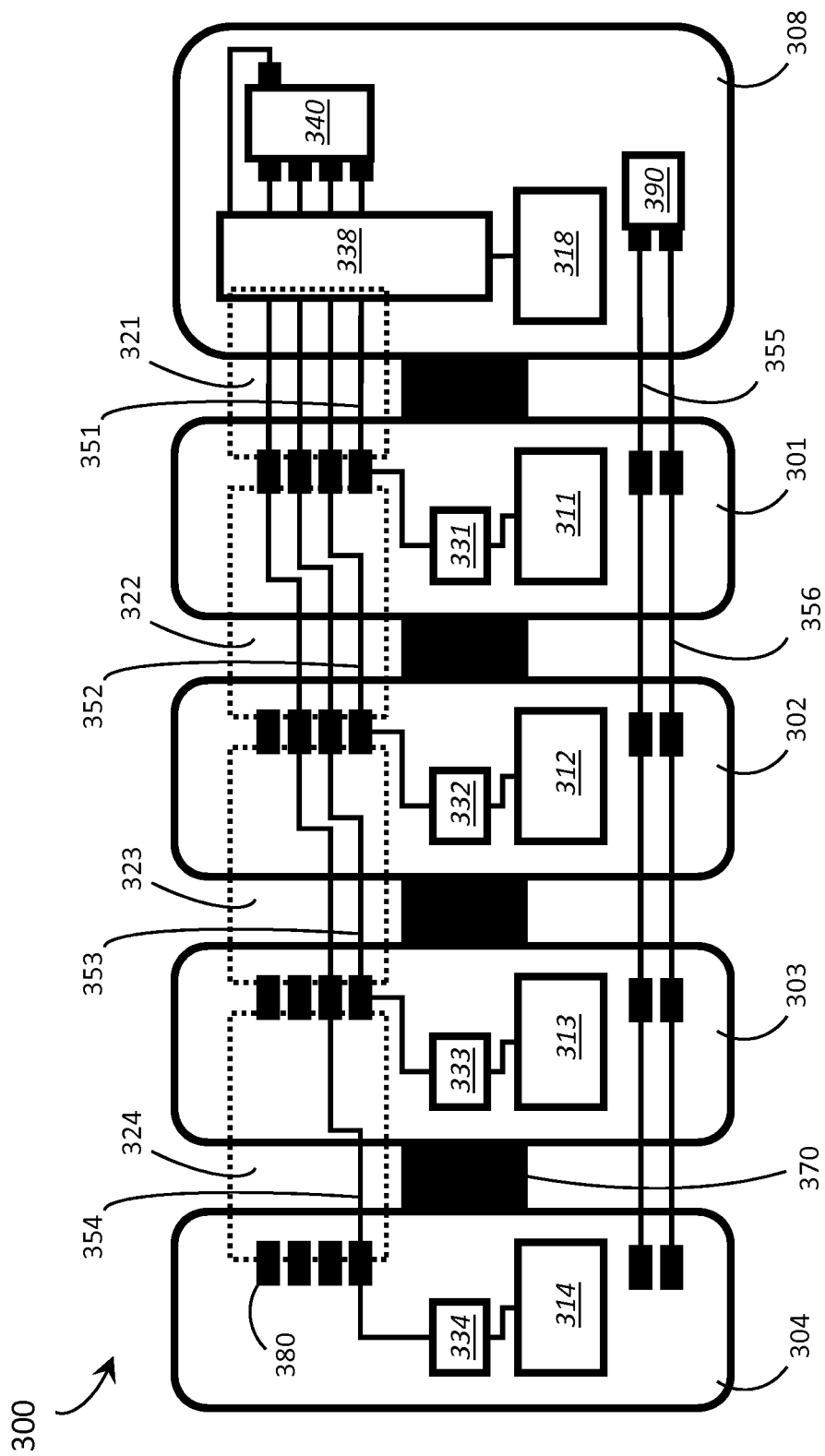
FIG. 3 is an illustrative diagram of a portion of a wearable electronic device showing exemplary routing of analog signals in accordance with the present systems, articles, and methods.

FIG. 3 is an illustrative diagram of a portion of a wearable electronic device 300 showing exemplary routing of analog signals in accordance with the present systems, articles, and methods. Device 300 is substantially similar to device 200 from FIG. 2 (and therefore also similar to device 100 from FIG. 1), though FIG. 3 only depicts a portion of device 300 that comprises four sensor pods 301, 302, 303, and 304 and a processor pod 308, all of which are serially communicatively coupled to route analog signals from sensor pods 301, 302, 303, and 304 to processor pod 308. Sensor pods 301, 302, 303, and 304 and processor pod 308 are all also adaptively physically coupled together by at least one adaptive coupler 370.

Each of sensor pods 301, 302, 303, and 304 comprises a respective sensor (e.g., a respective electromyography sensor) 311, 312, 313, and 314 communicatively coupled to respective electric circuitry 331, 332, 333, and 334. In use, sensors 311, 312, 313, and 314 detect inputs effected by a user and provide analog electrical signals in response to the detected inputs. The analog signals provided by each of sensors 311, 312, 313, and 314 are routed to electric circuitries 331, 332, 333, and 334, respectively. Each of electric circuitries 331, 332, 333, and 334 includes a respective amplification circuit to in use amplify the analog signals, and the amplified analog signals are serially routed via successively adjacent ones of sensor pods 301, 302, 303, and 304 to processor pod 308. Processor pod 308 has electric circuitry 338 that includes an ADC circuit to in use convert the amplified analog signals from sensor pods 301, 302, 303, and 304 into digital signals. The digital signals are routed to a processor 340 within processor pod 308. As previously described, processor 340 may include any type of processor (including but not limited to a digital microprocessor, a digital microcontroller, an FPGA, etc.) that analyzes the digital signals to determine at least one output, action, or function based on the digital signals. Processor 340 may include and/or be coupled to a computer-readable, non-transitory storage medium or memory storing instructions for how to process the digital signals.

In device 300, processor pod 308 also includes a sensor (e.g., an electromyography sensor) 318 to in use detect user-effected inputs and provide analog signals in response to the detected inputs. Sensor 318 is communicatively coupled to electric circuitry 338 in processor pod 308, and electric circuitry 338 includes an amplification circuit to in use amplify the analog signals provided by sensor 318. The amplified analog signals are then converted into digital signals by the ADC circuit in electric circuitry 338 and the digital signals are routed to processor 340.

The portion of device 300 shown in FIG. 3 provides an illustrative example of routing analog signals from a set of sensor pods 301, 302, 303, and 304 to a processor pod 308 within a wearable electronic device. In the illustrative example, analog signals are routed from sensor pods 301, 302, 303, and 304, respectively, through a set of four communicative pathways 351, 352, 353, and 354. Specifically: sensor pod 301 provides amplified analog signals to processor pod 308 via communicative pathway 351, sensor pod 302 provides amplified analog signals to processor pod 308 via communicative pathway 352, sensor pod 303 provides amplified analog signals to processor pod 308 via communicative pathway 353, and sensor pod 304 provides amplified analog signals to processor pod 308 via communicative pathway 354. Each of communicative pathways 351, 352, 353, and 354 may include one or more respective portion(s) depending on the number of intervening pod structures via which each communicative pathway passes en route from the corresponding sensor pod (301, 302, 303, or 304) to processor pod 308. In the illustrated example, communicative pathway 351 routes amplified analog signals from sensor pod 301 to processor pod 308 without passing via any intervening sensor pod(s) (because sensor pod 301 is positioned immediately adjacent processor pod 308), therefore communicative pathway 351 includes only a single portion that extends through region 321 that physically separates sensor pod 301 and processor pod 308. However, communicative pathway 352 routes amplified analog signals via sensor pod 301 en route from sensor pod 302 to processor pod 308, and accordingly, communicative pathway 352 includes a first portion that extends through region 322 that physically separates sensor pod 302 and sensor pod 301 and a second portion that extends through region 321. Depending on the implementation, communicative pathway 352 may or may not electrically couple to one or more component(s) of sensor pod 301 en route from sensor pod 302 to processor pod 308. Similarly, communicative pathway 353 routes amplified analog signals via sensor pod 302 and sensor pod 301 en route from sensor pod 303 to processor pod 308, and accordingly, communicative pathway 353 includes a first portion that extends through region 323 that physically separates sensor pod 303 and sensor pod 302, a second portion that extends through region 322, and a third portion that extends through region 321. Depending on the implementation, communicative pathway 353 may or may not electrically couple to one or more component(s) of sensor pod 302 and/or sensor pod 301 en route from sensor pod 303 to processor pod 308. Likewise, communicative pathway 354 routes amplified analog signals via sensor pod 303, sensor pod 302, and sensor pod 301 en route from sensor pod 304 to processor pod 308, and accordingly, communicative pathway 354 includes a first portion that extends through region 324 that physically separates sensor pod 304 and sensor pod 303, a second portion that extends through region 323, a third portion that extends through region 322, and a fourth portion that extends through region 321. Depending on the implementation, communicative pathway 354 may or may not electrically couple to one or more component(s) of sensor pod 303, sensor pod 302, and/or sensor pod 301 en route from sensor pod 304 to processor pod 308. Processor pod 308 receives amplified analog signals from sensor pods 301, 302, 303, and 304 through communicative pathways 351, 352, 353, and 354 (respectively) and converts the amplified analog signals into digital signals by the ADC circuit in electric circuitry 338. Digital signals are routed within processor pod 308 from electric circuitry 338 to processor 340.

Each of communicative pathways 351, 352, 353, and/or 354 may comprise one or multiple communicative pathways. The portion of device 300 shown in FIG. 3 illustrates each of communicative pathways 351, 352, 353, and 354 as a single respective pathway (some of which comprise multiple portions as described above) to enhance descriptive clarity of device 300 and is not necessarily representative of the number of communicative pathways that may be implemented in practice. For example, in order to streamline manufacturing of device 300, each of regions 321, 322, 323, and 324 may comprise the same number of portions of communicative pathways such that the coupling between each pair of adjacent pod structures in device 300 is substantially the same regardless of the number of signal channels actually coupled therebetween. For example, for the portion of device 300 illustrated in FIG. 3, each of regions 321, 322, 323, and 324 may include four portions of communicative pathways even though only one pathway may be active in region 324 (corresponding to a first portion of pathway 354), only two pathways may be active in region 323 (corresponding to a second portion of pathway 354 and a first portion of pathway 353), and only three pathways may be active in region 322 (corresponding to a third portion of pathway 354, a second portion of pathway 353, and a first portion of pathway 352). Employing the same number of communicative pathways/portions of communicative pathways in each of regions 321, 322, 323, and 324 regardless of the number of actual signal channels being coupled allows substantially the same coupling configuration to be used between each pair of pod structures in device 300, which in turn means that the coupling between each pair of pod structures in device 300 may be manufactured in substantially the same way. In other words, the manufacturing process for device 300 does not need to include pod-specific coupling configurations, pathways, and/or processes. Manufacturing costs are reduced by minimizing the number of steps in the manufacturing process, by minimizing the number of component-specific adaptations required for each manufacturing step, and/or by minimizing the number of distinct components. Thus, employing a single configuration for the coupling in each of regions 321, 322, 323, and 324 means that the coupling between each respective pair of pod structures may be realized by substantially the same physical component(s). Such reduces manufacturing costs by avoiding pod-specific adaptations for each communicative pathway and/or coupling configuration between pod structures.

As previously described, each of communicative pathways 351, 352, 353, and 354 may be physically realized in a variety of different ways, including but not limited to: electrically conductive wires/cables, ribbon cables, fiber-optic cables, optical/photonic waveguides, and/or electrically conductive traces on a printed circuit board. In the case of electrically conductive traces on a printed circuit board, a flexible printed circuit board may be advantageous over a rigid printed circuit board to accommodate the limited motion afforded by adaptive coupler 370. Thus, in some implementations each of communicative pathways 351, 352, 353, and 354 may comprise a respective flexible printed circuit board. In other implementations, each of regions 321, 322, 323, and 324 may include a respective flexible printed circuit board where the number of electrically conductive traces carried by (i.e., carried on and/or within) each respective flexible printed circuit board may be greater than or equal to the number of communicative pathways that include a respective portion in that region. Thus, for example, region 321 may include a flexible printed circuit board having four electrically conductive traces (a first trace corresponding to pathway 351, a second trace corresponding to the second portion of pathway 352, a third trace corresponding to the third portion of pathway 353, and a fourth trace corresponding to the fourth portion of pathway 354) and, as another example, region 324 may include a flexible printed circuit board having either one trace (corresponding to the first portion of pathway 354) or four traces (with a first trace corresponding to the first portion of pathway 354 and the other three traces being unused but included for the purpose of simplifying manufacturing by using the same flexible printed circuit board to couple in between pod structures regardless of the number of pathways/portions of pathway that extend between the pod structures). Each flexible printed circuit board may electrically couple to a respective socket (by, for example hot-bar soldering) in each of two adjacent pod structures in device 300. Such sockets are generally represented by terminals 380 in FIG. 3. Thus, each sensor pod 301, 302, 303, and 304 and processor pod 308 comprises a respective set of four terminals 380 (only one called out in FIG. 3 to reduce clutter). For the purpose of simplicity, each terminal 380 is used in FIG. 3 to embody both an input and an output functionality in device 300, though a person of skill in the art will appreciate that terminals 380 may employ physically separate and/or distinct input and output terminals that are communicatively coupled together through electrical and/or optical circuitry. In alternative embodiments, any or all of pathways 351, 352, 353, and/or 354 may extend via an intervening pod structure (en route to processor pod 308) without electrically coupling to any component thereof.

In device 300, successively adjacent pod structures are effectively daisy-chained together through communicative pathways 351, 352, 353, and 354. The illustrative diagram of FIG. 3 shows that communicative pathways 351, 352, 353, and/or 354 in some or each of regions 321, 322, 323, and 324 may be "staggered," "shifted, or "offset" such that a first input terminal 380 in each sensor pod is communicatively coupled to the corresponding sensor in that sensor pod and a first output terminal 380 in each sensor pod is communicatively coupled to a second input terminal 380 in an adjacent pod structure. For example, sensor pod 302 includes a first terminal 380 that is communicatively coupled to electric circuitry 332 to receive signals from sensor 312 and communicative pathway 352 includes: a first portion (extending through region 322) that communicatively couples between first terminal 380 in sensor pod 302 and a second terminal 380 in sensor pod 301 and a second portion (extending through region 321) that communicatively couples between second terminal 380 in sensor pod 301 and a third terminal 380 in processor pod 308. The shifting/offsetting of communicative connections between terminals 380 may be achieved by/within the communicative pathways themselves (as depicted in FIG. 3) by, for example, a corresponding routing of communicative pathways such as a corresponding layout of conductive traces in a flexible printed circuit board, or this shifting/offsetting may be achieved within each pod structure by, for example, corresponding communicative couplings between terminals 380. For example, in FIG. 3, each terminal 380 includes both an input and an output, though in alternative embodiments electrical and/or optical pathways may route signals between inputs and outputs of terminals 380.

Device 300 includes additional communicative pathways 355 and 356 that provide serial communicative coupling of power and ground lines through sensor pods 301, 302, 303, and 304 and processor pod 308. For example, processor pod 308 includes a battery 390 that is used to power wearable electronic device 300 and power is routed from processor pod 308 to sensor pods 301, 302, 303, and 304 through communicative pathways 355 and 356.

FIG. 3 shows exemplary device 300 that serially routes analog signals from four sensor pods 301, 302, 303, and 304 to one processor pod 308. Each analog signal is routed through a corresponding dedicated signal channel (i.e., a corresponding communicative pathway 351, 352, 353, and 354, respectively). For example, since sensor pod 301 routes amplified analog signals from each of sensor pods 301, 302, 303, and 304 to processor pod 308, at least four analog signal channels couple from sensor pod 301 to processor pod 308 through region 321. As previously described, manufacturing of device 300 can be simplified by providing substantially the same coupling configuration between each pair of adjacent pod structures; therefore, the number of communicative pathways in each of regions 321, 322, 323, and 324 is equal to the number of sensor pods 301, 302, 303, and 304 (i.e., four) that are serially routed to processor pod 308. For this reason, each of regions 321, 322, 323 and 324 may include four communicative pathways and each of sensor pods 301, 302, 303, and 304 may includes at least four terminals 380 for electrically coupling to/from corresponding ones of the four communicative pathways.

Routing of analog signals as exemplified by device 300 may be advantageous for some applications, but in accordance with the present systems, articles, and methods, other applications may benefit from routing digital signals instead of analog signals. Routing digital signals may be done using fewer signal channels than routing analog signals, and may provide improved robustness against noise and other forms of signal degradation.

Figure 4:
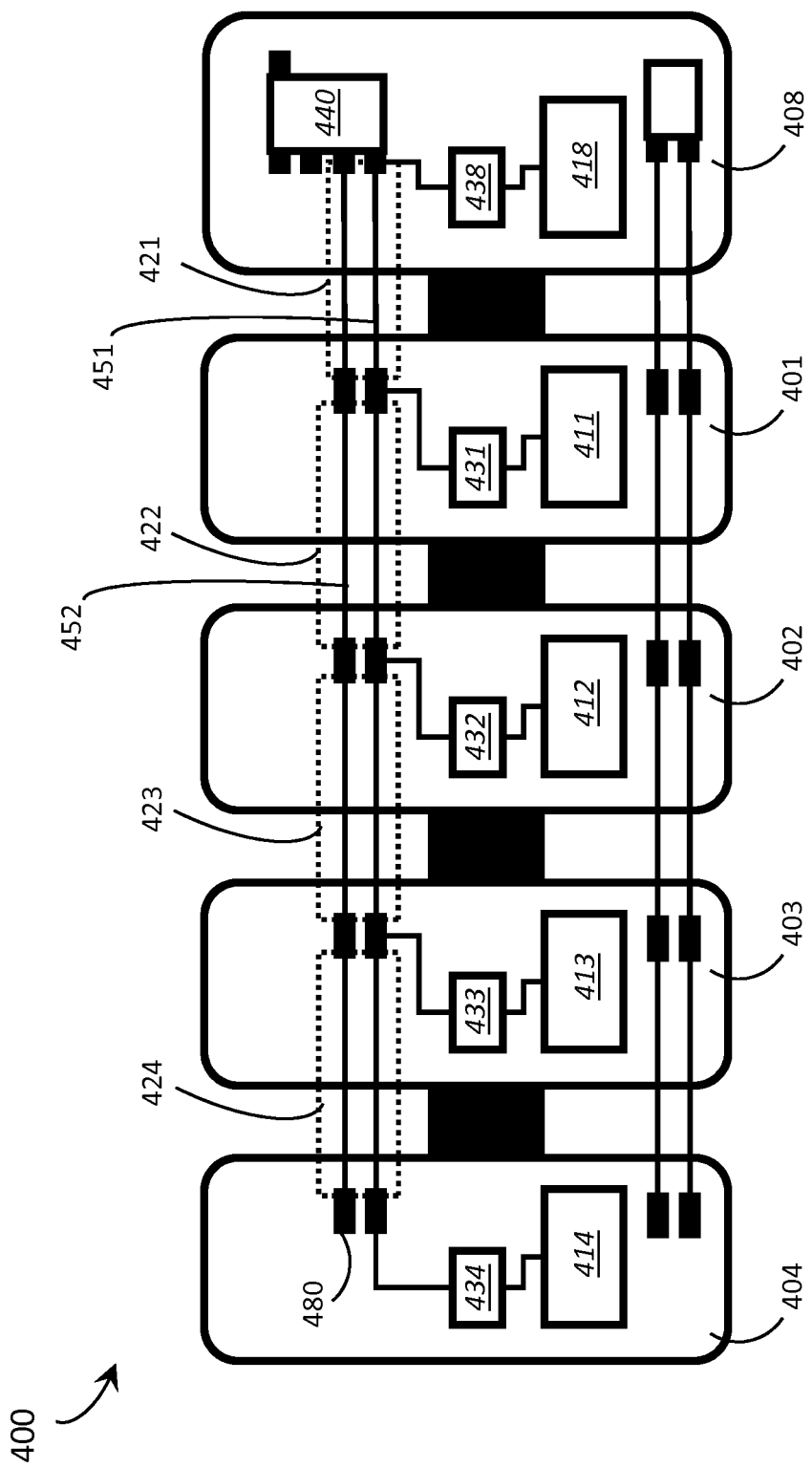
FIG. 4 is an illustrative diagram of a portion of a wearable electronic device showing exemplary routing of digital signals in accordance with the present systems, articles, and methods.

FIG. 4 is an illustrative diagram of a portion of a wearable electronic device 400 showing exemplary routing of digital signals in accordance with the present systems, articles, and methods. Device 400 is substantially similar to device 300 from FIG. 3 (and therefore also similar to device 200 from FIG. 2 and device 100 from FIG. 1) except that device 400 is designed to route digital signals between pod structures as opposed to analog signals. FIG. 4 only depicts a portion of device 400 that comprises four sensor pods 401, 402, 403, and 404 and a processor pod 408, all of which are serially coupled together to route digital signals from sensor pods 401, 402, 403, and 404 to processor pod 408.

Each of sensor pods 401, 402, 403, and 404 comprises a respective sensor (e.g., a respective electromyography sensor) 411, 412, 413, and 414 communicatively coupled to respective electric circuitry 431, 432, 433, and 434. In use, sensors 411, 412, 413, and 414 detect inputs effected by a user and provide analog signals in response to the detected inputs. The analog signals provided by each of sensors 411, 412, 413, and 414 are communicatively routed to electric circuitries 431, 432, 433, and 434, respectively. Each of electric circuitries 431, 432, 433, and 434 includes a respective amplification circuit to, in use, amplify the analog signals. Furthermore, each of electric circuitries 431, 432, 433, and 434 also includes a respective ADC circuit to, in use, convert the amplified analog signals into digital signals. The resulting digital signals are serially routed via successively adjacent ones of sensor pods 401, 402, 403, and 404 to processor pod 408. The digital signals are communicatively routed to a processor 440 within processor pod 408 that, in use, determines at least one output, action, or function based on the digital signals.

In device 400, processor pod 408 also includes a sensor (e.g., an electromyography sensor) 418 to, in use, detect user-effected inputs and provide analog signals in response to the detected inputs. Sensor 418 is communicatively coupled to electric circuitry 438 in processor pod 408, and electric circuitry 438 includes an amplification circuit to, in use, amplify the analog signals provided by sensor 418 and an ADC circuit to, in use, convert the amplified analog signals into digital signals. The digital signals are routed to processor 440 within processor pod 408.

The portion of device 400 shown in FIG. 4 provides an illustrative example of routing digital signals from a set of sensor pods 401, 402, 403, and 404 to a processor pod 408 within a wearable electronic device. In the illustrative example: sensor pod 404 outputs digital signals corresponding to signals provided by sensor 414 towards sensor pod 403 through a first portion of a digital signal bus 451 extending through region 424 that physically separates sensor pod 404 and sensor pod 403; sensor pod 403 receives digital signals from sensor pod 404 through the first portion of digital signal bus 451 and outputs both the digital signals received from sensor pod 404 and digital signals corresponding to signals provided by sensor 413 towards sensor pod 402 through a second portion of digital signal bus 451 extending through region 423 that physically separates sensor pod 403 and sensor pod 402; sensor pod 402 receives digital signals from sensor pod 403 (corresponding to signals provided by sensor 414 and signals provided by sensor 413) through the second portion of digital signal bus 451 and outputs both the digital signals received from sensor pod 403 and digital signals corresponding to signals provided by sensor 412 towards sensor pod 401 through a third portion of digital signal bus 451 extending through region 422 that physically separates sensor pod 402 and sensor pod 401; sensor pod 401 receives digital signals from sensor pod 402 (corresponding to signals provided by sensors 414, 413, and 412) through the third portion of digital signal bus 451 and outputs both the digital signals received from sensor pod 402 and digital signals corresponding to signals provided by sensor 411 towards processor pod 408 through a fourth portion of digital signal bus 451 extending through region 421 that physically separates sensor pod 401 and processor pod 408. Processor pod 408 receives digital signals from sensor pod 401 (corresponding to signals provided by sensors 414, 413, 412, and 411) through the fourth portion of digital signal bus 451 and routes the digital signals to processor 440.

In device 400, a single digital signal bus 451 communicatively couples to and between each of sensor pods 401, 402, 403, and 404 and processor pod 408. Timing and sequencing of respective digital signals in digital signal bus 451 from each of sensor pods 401, 402, 403, and 404 is controlled by a second communicative pathway that communicatively couples to and between each of sensor pods 401, 402, 403, and 404 and processor pod 408: a clock signal line 452. In accordance with the present systems, articles, and methods, digital signals may be routed between pod structures in device 400 using digital signal bus 451 and clock signal line 452 to implement any of a variety of known digital bus protocols, including but not limited to: I²C®, SMBus®, UNI/O®, 1-Wire®, HyperTransport®, etc., and/or using modifications or adaptations thereof.

FIG. 4 shows exemplary device 400 that serially routes digital signals from four sensor pods 401, 402, 403, and 404 to one processor pod 408. Unlike the analog signals routed in device 300, all of the digital signals may be transmitted through a single digital signal bus 451 and time-separated by clock pulses on a single clock line 452. Thus, routing of digital signals between pod structures may not use a corresponding dedicated channel for each digital signal. In device 400, each of regions 421, 422, 423, and 424 includes two communicative pathways: a respective portion of digital signal bus 451 and a respective portion of clock signal line 452, and each of sensor pods 401, 402, 403, and 404 comprises a set of two terminals 480. In accordance with the present systems articles, and methods, routing of digital signals between pod structures can be advantageous over routing of analog signals between pod structures because such allows fewer couplings between adjacent pod structures and because digital signals are inherently more robust against noise and signal degradation compared to analog signals.

A person of skill in the art will appreciate that the illustrative diagrams of FIGS. 3 and 4 show only some simplified electrical circuit and coupling (e.g., wiring) details and many electrical and coupling details are omitted. Any such simplifications and omissions are done solely for the purpose of enhancing clarity in conjunction with the corresponding descriptions in this specification. A person of skill in the art will appreciate that the simplification/omission of any component in any Figure is for the purpose of enhancing illustrative clarity only and in no way indicates the simplified/omitted component is somehow of lesser utility or value to the present systems, articles, and methods.

The present systems, articles, and methods describe routing signals between pod structures in a wearable electronic device comprising pod structures. FIGS. 1, 2, 3, and 4 provide illustrative examples of systems and articles that achieve such routing by implementing, for example, the method described in FIG. 5.

Figure 5:
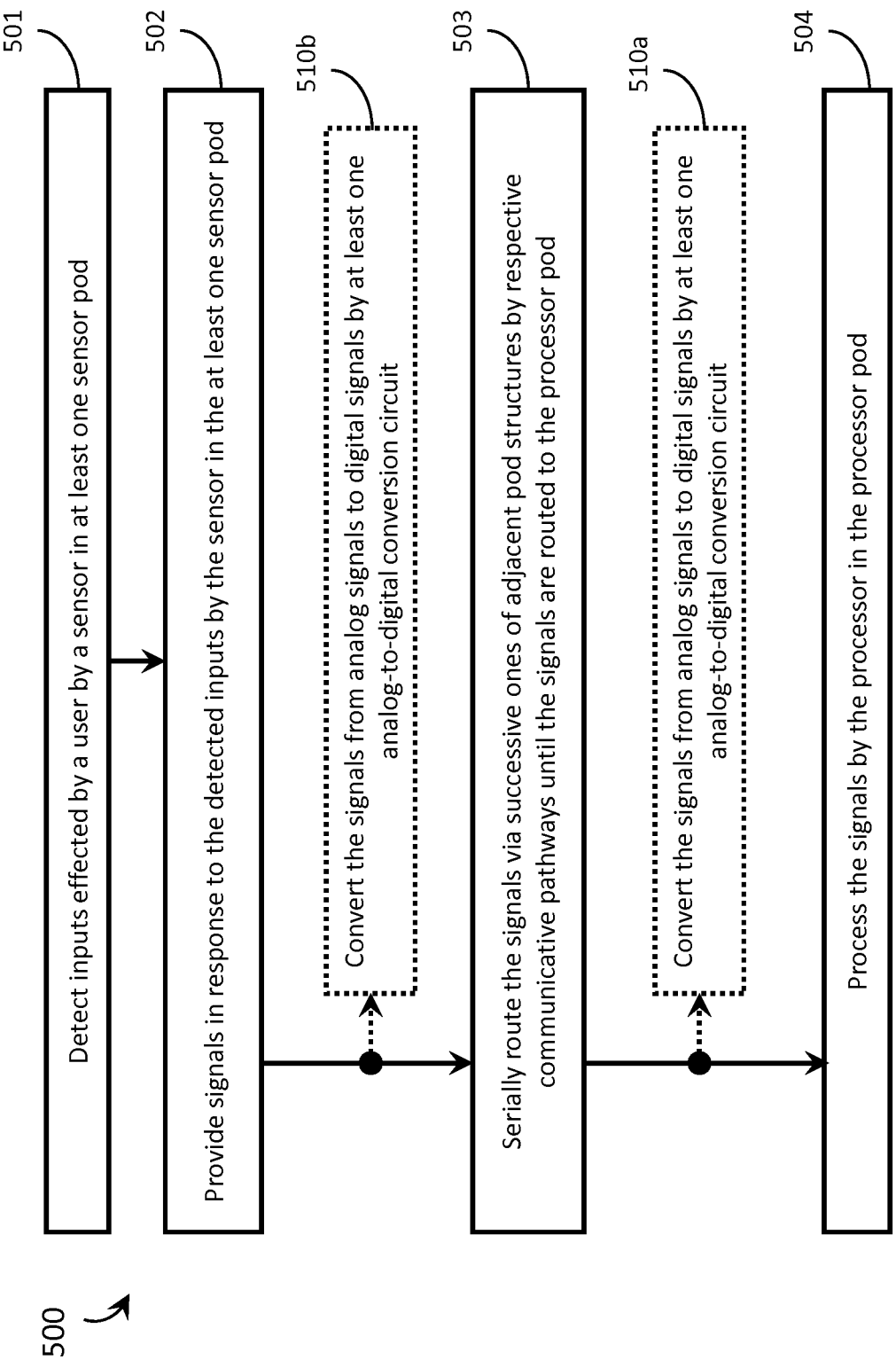
FIG. 5 is a flow-diagram showing a method of routing signals within a wearable electronic device in accordance with the present systems, articles, and methods.

FIG. 5 is a flow-diagram showing a method 500 of routing signals within a wearable electronic device in accordance with the present systems, articles, and methods. The wearable electronic device may include a plurality of pod structures including at least two sensor pods and a processor pod. In other words, the wearable electronic device may be substantially similar to device 100 from FIG. 1, device 200 from FIG. 2, and either device 300 from FIG. 3 or device 400 from FIG. 4. Method 500 includes four acts 501, 502, 503, and 504 and one optional act 510a/b, though those of skill in the art will appreciate that in alternative embodiments certain acts may be omitted and/or additional acts may be added. Those of skill in the art will also appreciate that the illustrated order of the acts is shown for exemplary purposes only and may change in alternative embodiments.

At 501, inputs effected by a user are detected by a sensor in at least one sensor pod of the wearable electronic device. The sensor may be an electromyography sensor and the inputs effected by the user may be muscle activity corresponding to a gesture performed by the user. The wearable electronic device may include a plurality of sensors distributed among a plurality of sensor pods and the user-effected inputs may be detected by at least one sensor (i.e., by one or more sensors) in at least one sensor pod (i.e., in one or more sensor pods).

At 502, signals are provided by the at least one sensor in the at least one sensor pod in response to the user-effected inputs. The signals may be amplified by at least one amplification circuit and/or filtered by at least one filtering circuit. The signals provided by the at least one sensor may be, for example, electrical signals.

At 503, the signals are serially routed via successive ones of adjacent pod structures in the wearable electronic device by respective communicative pathways until the signals are routed to the processor pod. The signals may be routed in, for example, electrical or optical form.

At 504, the signals are processed by a processor in the processor pod.

As previously described, the signals generated by each sensor may be analog signals and the analog signals may be amplified by a respective amplification circuit within each sensor pod. Method 500 also includes an optional act 510a/b that may be performed either after (i.e., 510a) or before (i.e., 510b) the serial routing of act 503 depending on whether the wearable electronic device routes analog signals or digital signals (i.e., depending on whether the wearable electronic device is substantially similar to device 300 from FIG. 3 or device 400 from FIG. 4).

If the wearable electronic device is substantially similar to device 300 from FIG. 3, then the device routes analog signals between pod structures and the processor pod includes an ADC circuit. In this configuration, method 500 may include act 510a after the serial routing of act 503. At 503, the analog signals are serially routed via successive ones of adjacent pod structures in the wearable electronic device by respective communicative pathways until the analog signals are routed to the processor pod. As described for device 300, analog signal routing may employ a number of communicative pathways that is equal to the number of serially-linked sensor pods. At 510a, the analog signals are converted to digital signals by the ADC circuit in the processor pod. At 504, the digital signals are processed by the processor in the processor pod.

If the wearable electronic device is substantially similar to device 400 from FIG. 4, then each pod structure includes a respective ADC circuit and the device routes digital signals between pod structures. In this configuration, method 500 may include act 510b before the serial routing of act 503. At 502, analog signals are provided by the at least one sensor in the at least one sensor pod in response to the user-effected inputs. At 510b, the analog signals are converted into digital signals by the respective ADC circuits in each sensor pod. At 503, the digital signals are serially routed via successive ones of adjacent pod structures in the wearable electronic device by respective communicative pathways until the digital signals are routed to the processor pod. As described for device 400, digital signal routing may employ two communicative pathways: one digital signal bus and one clock signal line. Digital signal routing may also employ any of a variety of known digital bus protocols, including but not limited to: I²C®, SMBus®, UNI/O®, 1-Wire®, Hyper-Transport®, etc., and/or using modifications or adaptations thereof. At 504, the digital signals are processed by the processor in the processor pod.

Throughout this specification and the appended claims, the term "provide" and variants such as "provided" and "providing" are frequently used in the context of signals. For example, an EMG sensor is described as "providing at least one signal." Unless the specific context requires otherwise, the term "provide" is used in a most general sense to cover any form of providing a signal, including but not limited to: relaying a signal, outputting a signal, generating a signal, routing a signal, creating a signal, transducing a signal, and so on. For example, a surface EMG sensor may include at least one electrode that resistively or capacitively couples to electrical signals from muscle activity. This coupling induces a change in a charge or electrical potential of the at least one electrode which is then relayed through the sensor circuitry and output, or "provided," by the sensor. Thus, the surface EMG sensor may "provide" an electrical signal by relaying an electrical signal from a muscle (or muscles) to an output (or outputs).

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," to, at least, provide," "to, at least, transmit," and so on.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other portable and/or wearable electronic devices, not necessarily the exemplary wearable electronic devices generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any computer-readable medium for use by or in connection with any processor-related system or method. In the context of this disclosure, a memory is a computer-readable medium that is an electronic, magnetic, optical, or other physical device or means that contains or stores a computer and/or processor program. Logic and/or the information can be embodied in any computer-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "non-transitory computer-readable medium" can be any element that can store the program associated with logic and/or information for use by or in connection with the instruction execution system, apparatus, and/or device. The computer-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to: U.S. Provisional Patent Application Ser. No. 61/866,960; U.S. Provisional Patent Application Ser. No. 61/857,105 (now U.S. Non-Provisional patent application Ser. No. 14/335,668); U.S. Provisional Patent Application Ser. No. 61/752,226 (now U.S. Non-Provisional patent application Ser. No. 14/155,107); U.S. Provisional Patent Application Ser. No. 61/768,322 (now U.S. Non-Provisional patent application Ser. No. 14/186,889); U.S. Provisional Patent Application Ser. No. 61/771,500 (now U.S. Non-Provisional patent application Ser. No. 14/194,252); and U.S. Provisional Application Ser. No. 61/860,063 (now U.S. Non-Provisional patent application Ser. No. 14/276,575), are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A wearable electronic device comprising:
a set of discrete and separately enclosed pod structures that form physically coupled links of the wearable electronic device, each pod structure in the set of discrete and separately enclosed pod structures positioned adjacent and physically coupled to at least one other pod structure in the set of pod structures, wherein the set of pod structures comprises:
(i) at least two sensor pods, each of the at least two sensor pods comprising a separate respective electromyography sensor configured to detect muscle activity by the user and provide signals in response to the detected muscle activity; and
(ii) a centralized processor pod comprising:
a central processor configured to process all signals provided by each of the at least two sensor pods; and
a plurality of communicative pathways configured to route signals provided by the at least two sensor pods to the centralized processor pod, wherein each of the at least two sensor pods is communicatively coupled to the centralized processor pod by at least one respective communicative pathway from the plurality of communicative pathways, and wherein the centralized processor of the centralized processor pod is adapted to analyze the signals that were provided in response to the detected muscle activity.

2. The wearable electronic device of claim 1, wherein each of the at least two sensor pods further comprises a respective amplification circuit configured to amplify signals provided by each separate respective electromyography sensor.

3. The wearable electronic device of claim 1, wherein the centralized processor pod comprises at least one analog-to-digital conversion ("ADC") circuit configured to convert analog signals provided by the at least two sensor pods into digital signals.

4. The wearable electronic device of claim 1, wherein the at least two sensor pods include a first sensor pod and a second sensor pod, the first sensor pod communicatively coupled to the centralized processor pod by a first communicative pathway from the plurality of communicative pathways and the second sensor pod communicatively coupled to the centralized processor pod by a second communicative pathway from the plurality of communicative pathways, and wherein:
the first communicative pathway comprises:
a first portion configured to route analog signals output by the first sensor pod to the centralized processor pod, and
the second communicative pathway comprises:
a first portion configured to route analog signals output by the second sensor pod to the first sensor pod, and
a second portion configured to route analog signals output by the second sensor pod from the first sensor pod to the centralized processor pod.

5. The wearable electronic device of claim 4, wherein the at least two sensor pods further includes a third sensor pod, the third sensor pod communicatively coupled to the centralized processor pod by a third communicative pathway from the plurality of communicative pathways, and wherein the third communicative pathway comprises:
a first portion configured to route analog signals output by the third sensor pod to the second sensor pod;
a second portion configure to route analog signals output by the third sensor pod from the second sensor pod to the first sensor pod; and
a third portion configured to route analog signals output by the third sensor pod from the first sensor pod to the centralized processor pod.

6. The wearable electronic device of claim 5, wherein the at least two sensor pods further includes a fourth sensor pod, the fourth sensor pod communicatively coupled to the processor pod by a fourth communicative pathway from the plurality of communicative pathways, and wherein the fourth communicative pathway comprises:
a first portion configured to route analog signals output by the fourth sensor pod to the third sensor pod;
a second portion configured to route analog signals output by the fourth sensor pod from the third sensor pod to the second sensor pod;
a third portion configured to route analog signals output by the fourth sensor pod from the second sensor pod to the first sensor pod; and
a fourth portion configured to route analog signals output by the fourth sensor pod from the first sensor pod to the centralized processor pod.

7. The wearable electronic device of claim 1, wherein each of the at least two sensor pods comprises a respective analog-to-digital conversion ("ADC") circuit configured to convert analog signals provided by each respective separate electromyography sensor into digital signals.

8. The wearable electronic device of claim 7, further comprising a clock signal line communicatively coupled to each pod structure in the set of pod structures and wherein the plurality of communicative pathways includes a digital signal bus that is communicatively coupled to the centralized processor pod, wherein the at least two sensor pods include a first sensor pod and a second sensor pod, the first sensor pod communicatively coupled to the digital signal bus by a first communicative pathway from the plurality of communicative pathways and the second sensor pod communicatively coupled to the digital signal bus by a second communicative pathway from the plurality of communicative pathways.

9. The wearable electronic device of claim 8, wherein the at least two sensor pods further includes a third sensor pod, the third sensor pod communicatively coupled to the digital signal bus by a third communicative pathway from the plurality of communicative pathways.

10. The wearable electronic device of claim 9, wherein the at least two sensor pods further includes a fourth sensor pod, the fourth sensor pod communicatively coupled to the digital signal bus by a fourth communicative pathway from the plurality of communicative pathways.

11. The wearable electronic device of claim 1, wherein the plurality of communicative pathways includes at least one power line and at least one ground line.

12. The wearable electronic device of claim 1, further comprising:
at least one adaptive coupler, wherein each respective pod structure in the set of pod structures is physically coupled to at least one adjacent pod structure in the set of pod structures by at least one extensible coupler.

13. The wearable electronic device of claim 1, wherein the centralized processor pod comprises:
an electromyography sensor configured to detect muscle activity by the user and provide signals in response to the detected muscle activity.

14. The wearable electronic device of claim 1, wherein the centralized processor pod further comprises:
- a sensor configured to detect inputs effected by the user and provide analog signals in response to the detected inputs;
- an amplification circuit configured to amplify analog signals provided by the sensor; and
- an analog-to-digital conversion ("ADC") circuit configured to convert analog signals into digital signals.

15. The wearable electronic device of claim 1, wherein each pod structure in the set of pod structures comprises a respective housing formed of a substantially rigid material and having a respective inner volume, and wherein:
- for each of the at least two sensor pods, the sensor is positioned on or proximate a surface of the housing,
- for the centralized processor pod, the central processor is positioned in the inner volume of the housing, and
- each communicative pathway in the plurality of communicative pathways includes a respective first portion in the inner volume of the housing of a respective first pod structure in the set of pod structures, a respective second portion in the inner volume of the housing of a respective second pod structure in the set of pod structures, and a respective third portion that extends between the housing of the respective first pod structure in the set of pod structures and the housing of the respective second pod structure in the set of pod structures.

16. The wearable electronic device of claim 1, wherein at least one communicative pathway in the plurality of communicative pathways is selected from the group consisting of: an electrically conductive pathway and an optical pathway.

17. The wearable electronic device of claim 1, wherein at least one communicative pathway in the plurality of communicative pathways comprises a flexible printed circuit board.

18. The wearable electronic device of claim 1, wherein each pod structure in the set of pod structures is positioned adjacent and in between two other pod structures in the set of pod structures and physically coupled to the two other pod structures in the set of pod structures, and wherein the set of pod structures forms a perimeter of an annular configuration.

19. The wearable electronic device of claim 1, wherein the processor of the centralized processor pod is adapted to determine a gesture of a user responsive to the analyzed signals in response to the detected muscle activity.

20. The wearable electronic device of claim 19, wherein the central processor of the centralized processor pod is adapted to determine the gesture of the user responsive to analyzed signals generated from the at least two sensor pods in response to the detected muscle activity.

21. The wearable electronic device of claim 1, wherein the at least two sensor pods are coupled to expand and contract around a user's body part.

22. The wearable electronic device of claim 21, wherein the at least two sensor pods are physically coupled by at least one of:
- at least one elastic band extending through the at least two sensor pods; and
- at least one elastic band coupling the at least two sensor pods.

23. The wearable electronic device of claim 22, wherein the at least two sensor pods are physically coupled with a strain mitigation element.

24. The wearable electronic device of claim 1, wherein the at least two sensor pods are configured to be positioned around a circumference of a user's body part.

25. The wearable electronic device of claim 24, wherein the circumference is a variable circumference and wherein the at least two sensor pods are physically coupled with an element that is resiliently expandable.

26. A non-transitory, computer-readable storage medium including instructions that, when executed by a wearable electronic device, cause the wearable electronic device to perform operations comprising:
- detecting inputs effected by a user by processing and analyzing signals associated with muscle activity by the user, wherein the wearable electronic device includes:
  - a set of discrete and separately enclosed pod structures that form physically coupled links of the wearable electronic device, wherein the set of pod structures comprises:
    - (i) a plurality of sensor pods, each sensor pod of the plurality of sensor pods comprising: a separate respective sensor configured to detect inputs effected by a user and provide signals in response to the detected inputs, wherein, for each of the plurality of sensor pods, the respective sensor comprises an electromyography sensor to detect the muscle activity by the user and provide signals in response to the muscle activity; and
    - (ii) a centralized processor pod comprising: a central processor configured to process all signals provided by the plurality of sensor pods, wherein each pod structure in the set of discrete and separately enclosed pod structures is positioned adjacent and physically coupled to at least one other pod structure in the set of pod structures, and
  - the wearable electronic device further includes:
    - a plurality of communicative pathways configured to route signals provided by the plurality of sensor pods to the centralized processor pod,
    - each pod structure in the set of discrete and separately enclosed pod structures is communicatively coupled to at least one adjacent pod structure in the set of pod structures by a respective communicative pathway from the plurality of communicative pathways configured to serially route signals provided by a respective sensor pod to the centralized processor pod via successive ones of adjacent pod structures in the set of pod structures, and
    - wherein the central processor of the centralized processor pod is configured to analyze the signals in response to the muscle activity.

27. The non-transitory, computer-readable storage medium of claim 26, wherein the plurality of sensor pods comprises:
- a first sensor pod positioned adjacent and physically coupled to the centralized processor pod;
- a second sensor pod positioned adjacent and physically coupled to the centralized processor pod;
- a third sensor pod positioned adjacent and physically coupled to the first sensor pod; and
- a fourth sensor pod positioned adjacent and physically coupled to the second sensor pod;

and wherein:
- the first sensor pod is communicatively coupled to the centralized processor pod by a first communicative pathway in the plurality of communicative pathways configured to route signals provided by the first sensor pod to the centralized processor pod;

the second sensor pod is communicatively coupled to the centralized processor pod by a second communicative pathway in the plurality of communicative pathways configured to route signals provided by the second sensor pod to the centralized processor pod;

the third sensor pod is communicatively coupled to the centralized processor pod by a third communicative pathway in the plurality of communicative pathways configured to route signals output by the third sensor pod from the third sensor pod via the first sensor pod to the centralized processor pod; and the fourth sensor pod is communicatively coupled to the centralized processor pod by a fourth communicative pathway in the plurality of communicative pathways configured to route signals output by the fourth sensor pod from the fourth sensor pod via the second sensor pod to the centralized processor pod.

28. The non-transitory, computer-readable storage medium of claim 27 wherein the third communicative pathway includes at least a portion of the first communicative pathway and the fourth communicative pathway includes at least a portion of the second communicative pathway.

29. The non-transitory, computer-readable storage medium of claim 26 wherein the centralized processor pod further comprises an analog-to-digital conversion ("ADC") circuit configured to convert analog signals into digital signals.

30. The non-transitory, computer-readable storage medium of claim 26 wherein each sensor pod in the plurality of sensor pods further comprises a respective analog-to-digital conversion ("ADC") circuit configured to convert analog signals into digital signals.

31. The non-transitory, computer-readable storage medium of claim 26, wherein the plurality of communicative pathways includes at least one power line and at least one ground line.

32. The non-transitory, computer-readable storage medium of claim 26, further comprising:
at least one adaptive coupler, wherein each respective pod structure in the set of pod structures is physically coupled to at least one adjacent pod structure in the set of pod structures by at least one extensible coupler.

33. The non-transitory, computer-readable storage medium of claim 26 wherein the centralized processor pod further comprises a sensor configured to detect inputs effected by the user and provide signals in response to the detected inputs.

34. The non-transitory, computer-readable storage medium of claim 26, wherein each pod structure in the set of pod structures comprises a respective housing formed of a substantially rigid material and having a respective inner volume, and wherein:
for each sensor pod in the plurality of sensor pods, the sensor is positioned on or proximate a surface of the housing,
for the centralized processor pod, the central processor is positioned in the inner volume of the housing, and
each communicative pathway in the plurality of communicative pathways includes a respective first portion in the inner volume of the housing of a respective first pod structure in the set of pod structures, a respective second portion in the inner volume of the housing of a respective second pod structure in the set of pod structures, and a respective third portion that extends between the housing of the respective first pod structure in the set of pod structures and the housing of the respective second pod structure in the set of pod structures.

35. The non-transitory, computer-readable storage medium of claim 26 wherein at least one communicative pathway in the plurality of communicative pathways is selected from the group consisting of: an electrically conductive pathway and an optical pathway.

36. The non-transitory, computer-readable storage medium of claim 26, wherein at least one communicative pathway in the plurality of communicative pathways comprises a flexible printed circuit board.

37. The non-transitory, computer-readable storage medium of claim 26, wherein each pod structure in the set of pod structures is positioned adjacent and in between two other pod structures in the set of pod structures and physically coupled to the two other pod structures in the set of pod structures, and wherein the set of pod structures forms a perimeter of an annular configuration.

38. A method of operating a wearable electronic device that comprises a set of discrete and separately enclosed pod structures and a plurality of communicative pathways, the set of pod structures including:
(i) a plurality of sensor pods, wherein each sensor pod in the plurality of sensor pods comprises a separate respective sensor, wherein each pod structure in the set of pod structures is positioned adjacent and physically coupled to at least one other pod structure in the set of pod structures,
(ii) a centralized processor pod comprising a central processor configured to process all signals provided by the plurality of sensor pods,
the method comprising:
detecting inputs effected by a user by a respective sensor in at least one sensor pod in the plurality of sensor pods;
providing signals in response to the detected inputs by the respective sensor in the at least one sensor pod in the plurality of sensor pods, and wherein the respective sensor comprises an electromyography sensor to detect muscle activity by the user and provide signals in response to detected muscle activity;
serially routing the signals via successive ones of adjacent pod structures in the set of pod structures by respective communicative pathways in the plurality of communicative pathways until the signals are routed to the centralized processor pod; and
processing and analyzing the signals in response to detected muscle activity by the central processor in the centralized processor pod.

39. The method of claim 38, wherein:
providing signals in response to the detected inputs by the sensor in the at least one sensor pod in the plurality of sensor pods includes providing analog signals in response to the detected inputs by the respective sensor in the at least one sensor pod in the plurality of sensor pods,
serially routing the signals via successive ones of adjacent pod structures in the set of pod structures by respective communicative pathways in the plurality of communicative pathways until the signals are routed to the centralized processor pod includes serially routing the analog signals via successive ones of adjacent pod structures in the set of pod structures by respective communicative pathways in the plurality of communicative pathways until the analog signals are routed to the centralized processor pod, and the centralized processor pod further comprises an analog-to-digital conversion ("ADC") circuit, and wherein the method further comprises:
converting the analog signals into digital signals by the ADC circuit in the centralized processor pod, wherein processing the signals by the central processor in the centralized processor pod includes processing the digital signals by the central processor in the centralized processor pod.

40. The method of claim 38, wherein providing signals in response to the detected inputs by the respective sensor in the at least one sensor pod in the plurality of sensor pods includes providing analog signals in response to the detected inputs by the respective sensor in the at least one sensor pod in the plurality of sensor pods, and wherein each sensor pod in the plurality of sensor pods further comprises a respective analog-to-digital conversion ("ADC") circuit, the method further comprising:
converting the analog signals provided by the respective sensor in the at least one sensor pod in the plurality of sensor pods into digital signals by the ADC circuit in the at least one sensor pod in the plurality of sensor pods, wherein:
serially routing the signals via successive ones of adjacent pod structures in the set of pod structures by respective communicative pathways in the plurality of communicative pathways until the signals are routed to the centralized processor pod includes serially routing the digital signals via successive ones of adjacent pod structures in the set of pod structures by respective communicative pathways in the plurality of communicative pathways until the digital signals are routed to the centralized processor pod, and processing the signals by the central processor in the centralized processor pod includes processing the digital signals by the central processor in the centralized processor pod.

41. The method of claim 38, wherein the respective sensor in each sensor pod in the plurality of sensor pods includes an electromyography sensor, and wherein detecting inputs effected by a user by the respective sensor in at least one sensor pod in the plurality of sensor pods includes detecting muscle activity of the user by the electromyography sensor in at least one sensor pod in the plurality of sensor pods and providing signals in response to the detected inputs by the respective sensor in the at least one sensor pod in the plurality of sensor pods includes providing signals in response to muscle activity of the user by the electromyography sensor in the at least one sensor pod in the plurality of sensor pods.

* * * * *